(12) United States Patent
Ben-Sasson et al.

(10) Patent No.: US 7,683,031 B2
(45) Date of Patent: Mar. 23, 2010

(54) SHORT PEPTIDES FROM THE '$2^{nd}$ LOOP' OF 7 TRANSMEMBRANE RECEPTOR WHICH SELECTIVELY MODULATE SIGNAL TRANSDUCTION

(75) Inventors: Shmuel Ben-Sasson, Jerusalem (IL); Hadas Reuveni, D.N. Harei Yehuda (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 872 days.

(21) Appl. No.: 10/526,533

(22) PCT Filed: Sep. 3, 2003

(86) PCT No.: PCT/US03/27332

§ 371 (c)(1),
(2), (4) Date: Jan. 18, 2006

(87) PCT Pub. No.: WO2004/022576

PCT Pub. Date: Mar. 18, 2004

(65) Prior Publication Data

US 2006/0257869 A1 Nov. 16, 2006

Related U.S. Application Data

(60) Provisional application No. 60/407,290, filed on Sep. 3, 2002.

(51) Int. Cl.
*A61K 38/00* (2006.01)
(52) U.S. Cl. .......................................... 514/12; 530/300
(58) Field of Classification Search ........................ None
See application file for complete search history.

(56) References Cited

U.S. PATENT DOCUMENTS 6,130,067 A * 10/2000 Tsui ........................... 435/69.1
2001/0044130 A1 11/2001 Glucksmann et al.

FOREIGN PATENT DOCUMENTS

WO 93/03749 A1 3/1993

OTHER PUBLICATIONS

Martin, et al, "Potent peptide analogues of a G protein receptor-binding region obtained with a combinatorial library", The Journal of Biological Chemistry. (1996). 27(1):361-366.
Kelleher et al., Characterization of rhodopsin kinase purified from bovine rod outer segments, The Journal of Biological Chemistry, 265(5)2632-2639 (1990).
Krupnick et al., Arrestin-rhodopsin interaction multi-site binding delineated by peptide inhibition, The Journal of Biological Chemistry, 269(5)3226-3232 (1994).
Benovic et al., Synthetic peptides of the hamster β2-adrenoceptor as substrates and inhibitors of the β-adrenoceptor kinase, Er. J. Clin. Pharmac. 30:3S-12S (1990).
Varrault et al., 5-Hydroxytryptamine1A receptor synthetic peptides mechanisms of adenylyl cyclase inhibition, The Journal of Biological Chemistry, 269(24)16720-16725 (1994).
Timossi et al., Structural determinants in the second intracellular loop of the human follicle-stimulating hormone receptor are involved in Gs protein activation, Molecular and Cellular Endocrinology, 189:157-168 (2002).
Chung et al., NMR structure of the second intracellular loop of the α2A adrenergic receptor: Evidence for a novel cytoplasmic helix, Biochemistry, 41:3596-3604 (2002).
Jimenez-Cervantes et al., The Pro162 variant is a loss-of-function mutation of the human melanocortin 1 receptor gene, The Journal of Investigative Dermatology, 117(1)156-158(2001).
Lee et al., Vascular endothelial cell adherens junction assembly and morphogenesis induced by sphingosine-1-phosphate, Cell, 99:301-312 (1999).
Okada et al., Activation of rhodopsin: new insights from structural and biochemical studies, Trends in Biochemical Sciences, 26(5)318-324 (2001).
Ballesteros et al., G protein-coupled receptor drug discovery: Implications from the crystal structure of rhodopsin, Current Opinion in Drug Discovery and Development, Current Drugs, 4(5)561-574 (2001).

\* cited by examiner

*Primary Examiner*—Robert Landsman
*Assistant Examiner*—Gyan Chandra
(74) *Attorney, Agent, or Firm*—Browdy and Neimark, PLLC

(57) ABSTRACT

The present invention concerns compounds comprising, within short sequences from a specific regions of the 7TM receptor, that can modulate 7TM receptor-associated signal. The present invention further concerns methods for stimulation angiogenesis by administration of peptides derived from the EDG3 7TM-receptor.

16 Claims, 18 Drawing Sheets

| | | | | | | | | | | | | | | | | | | | | | | |
|---|---|---|---|---|---|---|---|---|---|---|---|---|---|---|---|---|---|---|---|---|---|---|
| EDG3 | | E | R | H | L | T | M | I | K | M | | R | P | Y | D | A | N | K | R | H | R | |
| R002L103 | | | | | | | | | | M | | R | P | Y | D | A | N | K | R | | | |
| R002L106 | | | | | | | | | | Nor-L | | R | P | Y | | N | A | | | | | |

Fig. 1A

| | | Sequence | | | | | | | | | | | | | | | | |
|---|---|---|---|---|---|---|---|---|---|---|---|---|---|---|---|---|---|---|
| Lop 2 b3-Adr | | D | R | Y | L | A | V | T | N | P | L | R | Y | G | A | L | V | T | K | R | C | |
| R013L101 | Myr-G | | | | | | | N | P | L | R | Y | G | A | L | V | T | | | | L101 |
| R013L102 | Myr-G | | | | | | | | | L | R | Y | G | A | L | V | T | K | | | L102 |
| R013L103 | Myr-G | | | | | | | | P | L | R | Y | G | A | L | V | T | | | | L103 |
| MC1 - R | | | | | | | | | | | | | | | | | | | | | |
| R001L115 | Myr-G | | | | | | | | | L | R | Y | H | S | I | M | T | | | | |
| R001L116 | Myr-G | | | | | | | | | L | R | Y | H | S | I | M | K | T | | | |
| K024H107 | Myr-G | | | | | | | | L | L | R | r | H | S | | | | | | | H107 |
| K024H124 | L-G | | | | | | | | L | L | R | r | H | S | I | | | | | | H124 |

PTX 100ng/ml

R002L103 20μM

No PTX

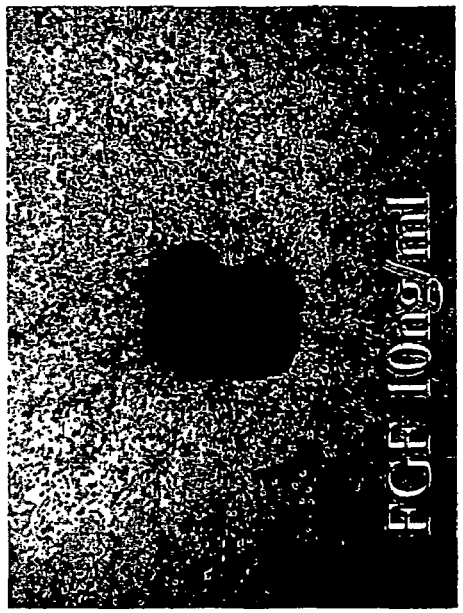
Fig. 8A control
Fig. 8B FGF 10ng/ml
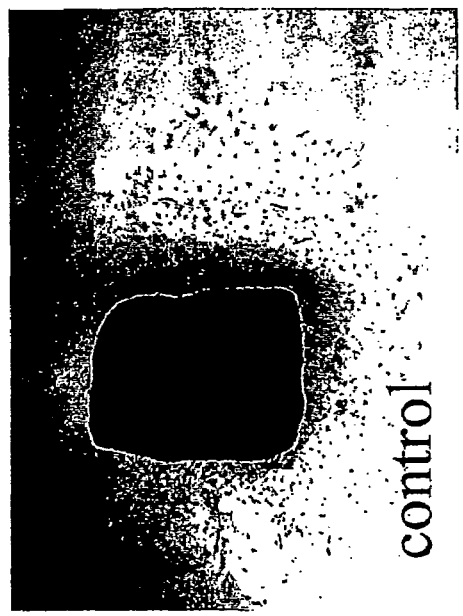
Fig. 8C R002L103 20uM
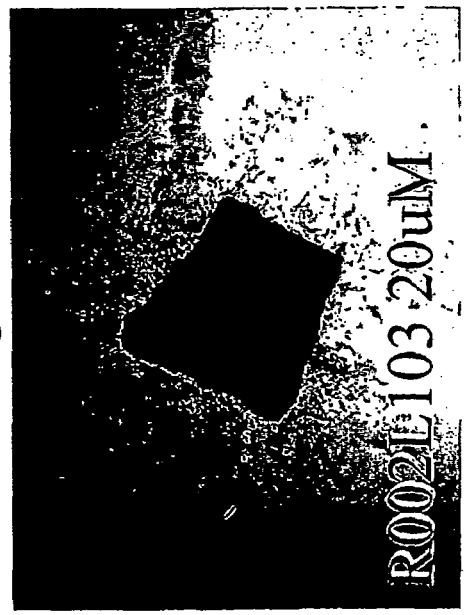
Fig. 8D R002L103+FGF

Fig. 9A control
Fig. 9B VEFG
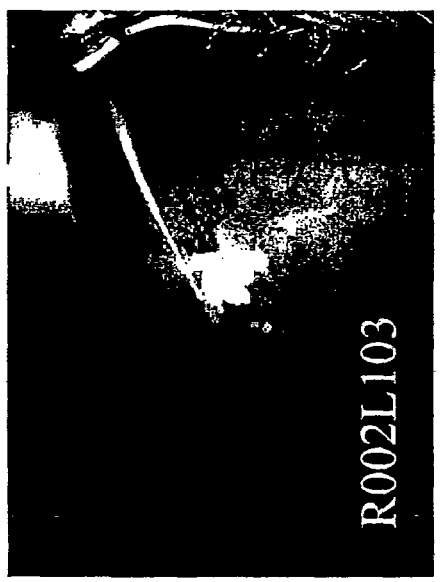
Fig. 9C R002L103

SHORT PEPTIDES FROM THE '2$^{nd}$ LOOP' OF 7 TRANSMEMBRANE RECEPTOR WHICH SELECTIVELY MODULATE SIGNAL TRANSDUCTION

FIELD OF THE INVENTION

The present invention concerns compounds for modulating 7 transmembrane associated signal transduction. The invention further concerns methods for using said compounds as well as methods for identifying and synthesizing said compounds.

BACKGROUND OF THE INVENTION

One of the largest families of receptors in the human genome is that of the 7 transmembrane receptor (7-TMR) superfamily, also known as G-protein coupled receptors (GPCRs), numbering approximately 2000. G-protein coupled receptors regulate a large number of important physiological processes. At least 40% of the prescription drugs that have been developed have actions related to these receptors. Most of these drugs work by interfering with the ligand binding to the receptor that occurs outside of cells. G-proteins are important effectors of cell activation.

There is now an effort in the scientific community to define compounds that block the intracellular interaction between the receptor and its signal transducing partner, the G-protein.

The second intracellular loop of the 7TMR receptors are known to play an important role in the signal transduction as mutations in this region cause a disturbance in the 7TMR-associated signal transduction.

There has been an attempt (Benovic et al., *Br. J. Clin. Pharmac.*, 30:3s-12s (1990) to interfere with the $\beta_2$-adrenoreceptor signal transduction by administration of peptides corresponding to the full second loop of this receptor. However, these results were extremely unsatisfactory as the sequence corresponding to the long 2$^{nd}$ loop was virtually inactive in modulating signal transduction with an IC$_{50}$ of about 240 μm.

Sphingosine 1-phosphate is formed in cells in response to diverse stimuli, including growth factors, cytokines, G-protein-coupled receptor agonists, antigen, etc. Its production is catalyzed by sphingosine kinase, while degradation is either via cleavage to produce palmitaldehyde and phosphoethanolamine or by dephosphorylation. Sphingosine 1-phosphate can also bind to members of the endothelial differentiation gene (EDG) G-protein-coupled receptor family [namely EDG1, EDG3, EDG5 (also known as H218 or AGR16), EDG6 and EDG8] to elicit biological responses. These receptors are coupled differentially via G(i), G(q), G(12/13) and Rho to multiple effector systems, including adenylate cyclase, phospholipases C and D, extracellular-signal-regulated kinase, c-Jun N-terminal kinase, p38 mitogen-activated protein kinase and non-receptor tyrosine kinases. These signaling pathways are linked to transcription factor activation, cytoskeletal proteins, adhesion molecule expression, caspase activities, etc. Therefore sphingosine 1-phosphate can affect diverse biological responses, including mitogenesis, differentiation, migration and apoptosis, via receptor-dependent mechanisms. Additionally, sphingosine 1-phosphate has been proposed to play an intracellular role, for example in Ca(2+) mobilization.

The term "angiogenesis" (also referred to at times as "neovascularization") is a general term used to denote the growth of new blood vessels both in normal and pathological conditions.

Angiogenesis is an important natural process that occurs during embryogenesis, and in the adult healthy body in the process of wound healing, and in restoration of blood flow back into injured tissues. In females, angiogenesis also occurs during the monthly reproductive cycle to build up the uterus lining and to support maturation of oocytes during ovulation, and in pregnancy when the placenta is formed, in the process of the establishment of circulation between the mother and the fetus. The healthy body controls angiogenesis through the interactions of angiogenesis-stimulating growth factors, and angiogenesis inhibitors, and the balance between the two determines whether angiogenesis is turned "on" or "off".

In the therapeutic field, there has been in recent years a growing interest in the control of angiogenesis. By one aspect, the aim was to control or diminish excessive and pathological angiogenesis that occurs in diseases such as cancer, diabetic blindness, age related macular degeneration, rheumatoid arthritis, psoriasis, and some additional 70 conditions. In these pathological conditions the new blood vessels feed the diseased tissue, for example the tumor tissue, providing it with essential oxygen and nutrients thus enabling its pathological growth. In addition the pathological angiogenesis many times destroys the normal tissue. Furthermore, the new blood vessels, formed for example in the tumor tissue, enable the tumor cells to escape into the circulation and metastasize in other organs. Typically, excessive angiogenesis occurs when diseased cells produce abnormal amounts of angiogenetic growth factors, overwhelming the effect of the natural angiogenesis inhibitors present in the body.

Anti-angiogenetic therapies developed today, are aimed at preventing new blood vessel growth through the targeting and neutralization of any of the stimulators that encourage the formation of new blood vessels.

A contrasting indication of regulating angiogenesis is the stimulation of production of neovascularization in conditions where insufficient angiogenesis occurs. Typically, these conditions are diseases such as coronary artery diseases, stroke, and delayed wound healing (for example in ulcer lesions). In these conditions, when adequate blood vessels growth and circulation is not properly restored, there is a risk for tissue death due to insufficient blood flow. Typically, insufficient angiogenesis occurs when the tissues do not produce adequate amounts of angiogenetic growth-factors, and therapeutic angiogenesis is aimed at stimulating new blood vessels' growth by the use of growth factors or their mimics.

The main goal of the angiogenesis therapy is to produce a biobypass—i.e. to physically bypass diseased or blocked arteries, by tricking the body into building new blood vessels.

SUMMARY OF THE INVENTION

The present invention is based on the discovery that compounds comprising relatively short sequences, identical to native sequences appearing in a specific region (hereinafter: "unique region") of the 2$^{nd}$ loop of 7 transmembrane receptor (hereinafter "7TM receptor"), or variants of said native sequences, are capable of altering the signal transduction mediated by the same 7TM receptor from which the sequences were obtained. Thus the invention leads to the discovery of compounds that can modulate a signal transduction associated with a 7TM receptor in a specific manner unique to said receptor.

Without wishing to be bound by theory, it is assumed that the compounds of the invention are active through one of several mechanisms. According to one mechanism the compounds bind to the 7TM receptor itself and by this increases or decreases directly the activity of the receptor. Decrease of the activity may be for example due to masking a domain required for interaction with other proteins, or by conferring an unfavorable conformational change in the 7TM receptor leading to decrease in the activity of the receptor. Increase of the activity, may be due, for example, to the induction of a conformational change in the receptor that renders it more active.

An alternative mechanism of action is based on the preferred assumption, in accordance with the invention, that the peptidic portion of the compound of the invention mimics a region in the $2^{nd}$ loop of the 7TM receptor which is responsible for the interaction of the receptor with other cellular components, such as with G-proteins, kinases, phosphatases or other kinases that phosphorylate or de-phosphorylate, respectively, the specific 7TM receptor or with other effectors of the 7TM receptor. This mimic sequence, when present in the compound of the invention, is then assumed to bind to the other cellular components with which the 7TMR interacts (not to the 7TM receptor) and by this interrupts the interaction of the receptor with the cellular components. Where originally the interaction between the 7TM receptor and the cellular component is an "on" interaction (for example the signal transduction resulting in increased transcription) said interruption causes inhibition of the signal transduction mediated by the 7TM receptor. Where the interaction between the 7TM receptor and the cellular component is a "off" reaction (for example signal transduction resulting in decreased transcription) said interruption of interaction decreases the "off" direction, resulting in an increase in signal transduction mediated by the 7TM receptor.

It has further been found in accordance with the invention that for the purpose of modulating the 7TM associated signal transduction, it is possible to prepare a compound comprising any one of several short subsequences appearing in the unique $2^{nd}$ loop region, or variants of the sequences having some alterations as compared to the native sequence. In accordance with the above assumption of the invention, the activity of the mimic sequence is to interrupt the interaction between the 7TM receptor and other cellular components. For such an interruption there is no need to faithfully copy the full region and mimicking of one of several optional sub-parts of the regions is sufficient. Furthermore it probably is sufficient merely to copy the overall structure of the region, as well as the chemical properties of those amino acids in the regions responsible for the protein-protein interaction, to obtain modulating properties. This explains the fact that many times a variant having many alterations as compared to the native sequence has the same, or even better modulating properties than the native sequence. The improvement in activity of the variant may be due for example to stabilization of a more favorable conformations.

Thus, the present invention allows for the first time a method for readily identifying compounds that are candidates for modulating signal transduction associated with 7TM receptors.

The present invention also enables obtaining compounds that can modulate said 7TM receptor-associated signal transduction, by testing the candidates, and selecting from the candidates only those compounds which modulated said 7TM receptor-associated signal transduction.

The present invention also concerns a method for the modulation of 7TM receptor-associated signal transduction comprising the administration of said compounds. This method may be used for the treatment of a plurality of diseases that are caused by, or are a result of non-normal 7TM-associated signal transduction.

The present invention also concern compounds for the modulation of 7TM receptor-associated signal transduction, as well as pharmaceutical compositions comprising these compounds.

The present invention also concerns the use of said compounds for the preparation of medicaments.

By another aspect, the present invention is based on the surprising finding that peptides which are derived from the $2^{nd}$ loop of EDG3 7-transmembrane receptor, or derivatives of said peptides, were able to encourage angiogenesis in a very significant manner.

Thus, the present invention by this aspect concerns a method for increase of angiogenesis by contacting blood vessels with an effective amount of a compound comprising a peptide derived from the $2^{nd}$ loop of EDG3 receptor.

GENERAL DESCRIPTION OF THE INVENTION

By one aspect, the present invention concerns a method for identifying candidate compounds for the modulation of signal transduction associated with a 7TM receptor, the method comprising:

(A) identifying a peptide region in the 7TM receptor ("unique region") by aligning $2^{nd}$ intracellular region of the 7TM receptor with the $2^{nd}$ intracellular region of rhodopsin and determining the sequence of the 7TM receptor corresponding to positions 143-151 of rhodopsin;

(B) synthesizing at least one compound comprising a sequence selected from:

(b1) a sequence comprising of from a minimum of 5 continuous amino acids of said unique region to a maximum of all the continuous amino acids of said unique region;

(b2) a variant of the sequence of (b1) wherein up to 40% of the amino acids of the sequence of (b1) have been replaced with a naturally or non-naturally occurring amino acid or with a peptidomimetic organic moiety; and/or up to 40% of the amino acids have their side chains chemically modified, and/or up to 20% of the amino acids have been deleted, provided that at least 50% of the amino acids of (b1) are maintained unaltered in the variant;

(b3) a sequence of (b1) or (b2) wherein one or more of the amino acids is replaced by the corresponding D-amino acid;

(b4) a sequence of any one of (b1) to (b3) wherein at least one peptidic backbone atom, or peptidic backbone bond has been altered to a modified peptidic backbone atom or a non-naturally occurring peptidic backbone bond, respectively;

(b5) a sequence of any one of (b1), (b2), (b3) or (b4) in a reverse order; and (b6) a combination of two or more of the sequences of (b1), (b2), (b3), (b4) or (b5).

(C) testing each compound of (b) to determine the capacity thereof to modulate the signal transduction associated with the 7TM receptor.

Preferably the unique region is a region corresponding to positions 142-147 of rhodopsin when the $2^{nd}$ intracellular loop of the 7TM receptor and the $2^{nd}$ intracellular region of rhodopsin are aligned.

The present invention also concerns a method for obtaining a compound for the modulation of 7TM receptor-associated signal transduction the method comprising:

(1) identifying candidate compounds for the modulation of 7TM receptor-associated signal transduction by the method as defined above;
(2) selecting from the candidate compounds those compounds which modulate signal transduction associated with the 7TM receptor in the test assay, as compared to the modulation in the same test assay in the absence of the candidate compound; and
(3) producing the selected compounds of (2) thereby obtaining compounds for the modulation of 7TM receptor-associated signal transduction.

The present invention also concerns compounds for the modulation of 7TM receptor-associated signal transduction obtained by the above method.

The present invention further concerns a method for modulating signal transduction associated with a 7TM receptor by administrating a compound obtained by any of the above methods.

The present invention still further concerns a method for the treatment of a disease, disorder or condition, wherein a therapeutically beneficial effect may be evident by the modulation of at least one signal transduction associated with a 7TM receptor comprising: administering to a subject in need of such treatment a therapeutically effective amount of the above compound.

By a second aspect termed "the angiogenesis aspect" the present invention concerns a method for increasing angiogenesis, by the administration of short peptides derived from the second loop of EDG3 7TM-receptor Thus, the present invention concerns a method for the stimulation of angiogenesis comprising: contacting blood vessels with an effective amount of a compound comprising a sequence selected from:
(a) a sequence which is a continuous stretch of at least 5 amino acids present in native EDG3 in positions of 135 to 154;
(b) a variant of the sequence according to (a) wherein up to 40% of the amino acids of the native sequence have been replaced with a naturally or non-naturally occurring amino acid or with a peptidomimetic moiety; and/or up to 40% of the amino acids have their cytokines chemically modified; and/or up to 20% of the amino acids have been deleted provided that at least 50% of the amino acids in the parent sequence of (a) are maintained unaltered and the variant, and provided that the variant has angiogenesis increasing properties;
(c) a sequence according to (a) or (b) wherein at least one of the amino acids is replaced with a corresponding D-amino acid;
(d) a sequence according to any one of (a)-(c) wherein at least one of the peptidic backbones has been altered to a non-naturally occurring peptidic backbone;
(e) a sequence being the sequence of any one of (a)-(d) in reverse order and;
(f) a combination of two or more of the sequences of (a) to (f).

Preferably the sequence of (a) is in positions 143-151 of EDG3 more preferably in positions 143-148. Examples of such compounds are ROO2L103 and R002L106 as specified in FIG. 1.

In accordance with this aspect, the method is used to increase angiogenesis for the purpose of prevention, treatment or alleviation of a disease or condition wherein a beneficial therapeutic effect may be evident by neovascularization (i.e.—angiogenesis formation of new blood vessels). Examples of such diseases are coronary artery diseases, peripheral artery diseases, endothelial vascular diseases, arthrosclerosis, various processes of wound and tissue healing such as healing of bone tendon endothelial lining (such as in ulcers in the stomach or skin), for improving the success rate of cell transplantation techniques, as well as in reconstructive surgery to help reestablish proper blood circulation to the reconstructed tissue.

The term "increase angiogenesis" concerns increase in the formation and/or growth rate of new blood vessels, as well as stabilization and/or elongation of existing blood vessels.

The term "EDG3" refers to EDG3_HUMAN, accession No Q99550 as appearing in NCBI.

The term "provided that at least 50% of the amino acid in the parent protein are maintained or unaltered" the up to 40% substitution, up to 40% chemical modification and up to 20% deletion are combinatorial, i.e. the same variant may have both substitutions chemical modifications and deletions as long as at least 50% of the native amino acids are identical to those of the $2^{nd}$ loop of the 7TM receptor. In the angiogenesis aspect of the invention the variant has to feature "increasing angiogenesis" properties that can be determined for example by one of the assays in the Detailed Description part of the specification.

Preferably at least 60, 65%, 70, 75%, 80, 85% in the parent sequence have to be maintained in the variant.

The term "signal transduction associated with the 7TM receptor" refers to the level of signaling of a specific signaling pathway wherein the specific 7TM receptor is one of the effectors of the signaling. The determination of the signal transduction is carried out by determination of a physiological property resulting from this signal transduction pathway. Said level of signaling may be determined directly by measuring the level of GTP production by the relevant G-protein, in a response to a given signal. The measurement may be also carried out by measuring other indirect biochemical, cellular or physiological properties which are changed as a result of the signal transduction associated with the 7TM receptor as will be explained in the Detailed Description part of the specification.

This modulation may be caused by a direct effects on the 7TM receptor itself (for example due to binding to the 7TM receptor) or alternatively and preferably, as explained above, the modulation may be caused by the interruption of the interaction of the 7TM receptor with various cellular components (such as G-proteins, cofactors, regulators, kinases and other phosphatases), by the binding of the compound to the cellular components, and said interruption may lead to the modulation in the signal transduction.

The term "modulating" (modulation to modulate etc.) refers to an increase, or decrease, in the level of the signal transduction associated with the 7TM receptor, as determined by any of the assays. For example, if the signal transduction is determined by assessing the level of GTP, modulation refers to increase, or decrease in the level of GTP as compared to the level of GTP in the same assay in the absence of the compound of the invention (or in the presence of a control compound).

The term "cellular components of the signal transduction" refers to the molecules that participate in the signal transduction in which the 7TM receptor is involved including: the receptor, other kinases, phosphatases (which phosphorylate, dephosphorylate the receptor, respectively), G-proteins (which may be also the same or other kinases) co-factors, and effector molecules.

The term "compound (comprising sequence)" refers to a compound that includes within any of the sequences of (b1) to (b6) as defined above. The compound may be composed mainly from amino acid residues, and in that case the amino acid component of the compounds should comprise no more than a total of about 55 amino acids. Where the compound is mainly an amino acid molecule, it may consist of any one of the amino acid sequences of (b1) to (b5) a combination of at least two, preferably three, most preferably of two, of the sequences of (b1) to (b5) linked to each other (either directly or via a spacer moiety) to give (b6). The compound may further comprise any one of the amino acids sequences, or combinations as described above (in (b1) to (b6) above), together with additional amino acids or amino acid sequences other than those of (b 1) to (b6). The additional amino acids may be sequences from other regions of the 7TM receptor, (or in accordance with the second aspect the EDG3 receptor) sequences that are present in the 7TM receptor in vicinity of the unique region, N-terminal or C-terminal to the sequences defined in (a), or sequences which are not present in the specific 7TM receptor but were included in the compound in order to improve various physiological properties such as: penetration into cells (sequences which enhance penetration through membranes); decreased degradation or clearance; decreased repulsion by various cellular pumps, improved immunogenic activities, improvement in various modes of administration (such as attachment of various sequences which allow penetration through various barriers such as the blood-brain barrier, through the gut, etc.); increased specificity, increased affinity, decreased toxicity, improved solubility moieties added for imaging purposes and the like. A specific example is the addition of the amino acid Gly or several Gly-residues in tandem to N-terminal of the sequence.

The compound may also comprise non-amino acid moieties, such as for example, hydrophobic moieties (various linear, branched cyclic, polycyclic or heterocyclic hydrocarbons and hydrocarbon derivatives) fatty acids associated to the peptides of (b1) to (b6) to improve penetration through membranes; various protecting groups, especially where the compound is a linear molecule, attached to the compound's terminals to decreased degradation; chemical groups present in the compound to improve penetration or decrease toxic side effects, or various spacers, placed for example, between one or more of the above amino acid sequences, so as to spatially position them in suitable order in respect of each other and the like. The compound of the invention may be a linear or cyclic molecule, and cyclization may take place by any means known in the art. Where the compound is composed predominantly of amino acids/amino acid sequences, cyclization may be N- to C-terminal, N-terminal to side chain and N-terminal to backbone, C-terminal to side chain, C-terminal to backbone, side chain to backbone and side chain to side chain, as well as backbone to backbone cyclization. Cyclization of the molecule may also take place through the non-amino acid organic moieties.

The association between the unique region-derived sequence (defined in (b1) to (b6)) and other components of the compound may be by covalent linking, or by non-covalent complexing, for example, by complexing to a hydrophilic polymer, which can be degraded or cleaved thereby producing a compound capable of sustained release (the cleavage may be inside the cell thus releasing the peptidic portion of the compound), by entrapping the peptidic part of the compound in liposomes or micelles to produce the final compound of the invention, by hydrostatic bonds, due to hydrogen bonds etc.

The term "a sequence comprising of from 5 continuous amino acids of said A-region to a maximum of . . . " means any continuous stretch of at least 5 amino acids, which are present in a longer amino acid sequence described by reference to positions 142-150, preferably 142-147 of rhodopsin (see below). In accordance with the angiogenesis aspect of the invention this term refers to short sequences present in positions 135-154 of EDG3 receptor. For example, if in a specific TM receptor such as EDG3, the positions corresponding to amino acid residues 142-150 in rhodopsin are 143-151 in the peptide, the continuous stretch of at least 5 amino acids may be from amino acid at position 143 to 147, from 144 to 148, from 145 to 149, etc. The continuous sequence may be of 5, 6, (for example 143-148, . . . 146 to 151), 7 (143-149 . . . , 145-151), 8, 9 amino acids. Preferably the sequences are of 6 amino acids.

The term "sequence corresponding to positions . . . to . . . of rhodopsin" refers to a sequence that is matches the sequence appearing in the native rhodopsin when the $2^{nd}$ intracellular loops of the two are aligned (or only the second loops are aligned). For determining the beginning and end positions of the specific 7TM receptor used, the sequence of the specific 7TM receptor should be aligned with the sequence of the $2^{nd}$ intracellular loop of rhodopsin in pair-wise or multiple-alignment manner. Alignment may be carried out using any state of the art software such as ClustA1™ (version W or X). In some 7TM receptor extra amino or less amino acids may be present in this region and the size of the unique region can, therefore, include more or less than 9 amino acids in length, however, the alignment methods (both present in ready table or carried out by known programs) can be carried out even if the size of the unique region of the 7TM receptor and the unique region are different. It shall be noted that when the 7TM receptor is rhodopsin itself the positions are already given.

The term "rhodopsin" refers to chain A structure of Bovine rhodopsin accession No. 1JFP_A, GI: 16975387 as appearing in NCBI.

The term "a variant wherein up to 40% of the amino acids of the native sequence have been replaced with a naturally or non-naturally occurring amino acid or with a peptidomimetic organic moiety" in accordance with the present invention, concerns a peptide, which corresponds in at least about 60% of its amino acid with the native sequence as described in (b1) above, but some (up to 40%) of the amino acids were replaced either by other naturally occurring amino acids, (both conservative and non-conservative substitutions), by non-naturally occurring amino acids (both conservative and non-conservative substitutions), or with organic moieties which serve either as true peptidomimetics (i.e. having the same steric and electrochemical properties as the replaced amino acid), or merely serve as spacers in lieu of a deleted amino acid, so as to keep the spatial relations between the amino acid spanning this replaced amino acid. Generally, essential amino acids as determined by various Structure-Activity-Relationship (SAR) techniques (for example amino acids host when replaced by Ala cause loss of activity) are replaced by conservative substitution while non essential amino acids can be deleted or replaced by any type of substitution. Guidelines for the determination of the deletions, replacements and substitutions are given in the detailed description part of the specification. Preferably no more than 35%, 30, 25% or 20% have been replaced.

The term "wherein up to 40% of the amino acids have their side chains chemically modified" refers to a variant which has the same type of amino acid residue as in the native sequence, but to its side chain a functional groups has been added. For example, the side chain may be phosphorylated, glycosylated, fatty acylated, acylated, iodinated or carboxyacylated. Other examples of chemical substitutions are known in the art and some are given below. Preferably no more than 35%, 30%, 25%, or 20% of the amino acids have their side chains chemically modified.

The term "up to 20% of the amino acids have been deleted" refer to an amino acid sequence which maintains at least 20% of its amino acid. Preferably no more than 10% of the amino acids are deleted and more preferably none of the amino acids are deleted.

The term "provided that at least 50% of the amino acids in the parent protein are maintained unaltered in the variants" the up to 40% substitution, up to 40% chemical modification and up to 20% deletions are combinatorial, i.e. the same variant may have substitutions, chemical modifications and deletions so long as at least 50% of the amino acids of the variant are identical (in nature and in position) to those of the native sequence. In addition, the properties of the parent sequence, in modulating 7TM receptor-associated signal transduction, have to be maintained in the variant typically at the same or higher level.

When calculating 40% (or 35, 30, 25, 20%) replacement of 20% (or 10%) deletion from sequences, the number of actual amino acids should be rounded mathematically, so that both 40% of an 11 mer sequence (4.4) and 40% of a 12 mer sequence (4.8) is five amino acids.

The term "at least one peptidic backbone atom or peptidic backbone bone have been chemically modified or altered to a non-naturally occurring peptidic backbone bond, respectively" means that the bond between the N— of one amino acid residue to the C— of the next has been altered to non-naturally occurring bonds by reduction (to —$CH_2$—NH—), alkylation (for example methylation) on the nitrogen atom, or the bonds have been replaced by a reduced bond such as an amine, urea bonds, or sulfonamide bond, etheric bond (—$CH_2$—O—), thioetheric bond (—$CH_2$—S—), or to —CS—NH—. The side chain of the residue may be shifted to the backbone nitrogen to obtain N-alkylated-Gly (a peptidoid). Preferably all the peptidic backbone has been altered to make the compound more resistant to degradation.

The term "where one or more of the amino acids is replaced by the corresponding D-amino acid" refers to replacement of a specific amino acid X in a normal L-configuration by the D-counterpart. In particular for producing "retro inverso" (see below).

The term "in reverse order" refers to the fact that the sequence of (b1), (b2) or (b3) or (b4) may have the order of the amino acids as it appears in the native receptor from N-C direction, or may have the reversed order (as read in the C- to N-direction) for example, if a continuous stretch of 5 amino acids from the unique region of EDG3 is MRPYDANKR (SEQ ID NO:1) a sequence in a reverse order is RKNADYPRM (SEQ ID NO:2). It has been found that many times sequences having such a reverse order can have the same properties in short peptides as the "correct" order, probably due to the fact that the side chains, and not the peptidic backbone are those responsible for the interactions. Particularly preferred, are what is termed "retro inverso" peptides— i.e. peptides that have both a reverse order as explained above, and in addition each and every single one of the amino acids, has been replaced by the non-naturally occurring D-amino acid counterpart, so that the net end result as regards the positioning of the side chains (the combination of reverse order and as the change from L to D) is zero change. Such retro-inverso peptides, while having similar binding properties to the native peptide, were found to be resistant to degradation.

The combination may be of two or more, more preferably three, most preferably two of the sequences of (b1) to (b5).

The N-terminus and/or C-terminus of these sequences present in the compounds can be modified, as described above and as shown in FIG. 1. The N-terminal of these peptides can be myristylated and the C-terminal is amidated. Other protecting groups for amides and carboxylic acids can be used, as will be described bellow. Optionally, one or both protecting groups can be omitted. The compounds may be linear or cyclic.

The signal transduction associated with the 7TM receptor in a subject can be modulated for treating a disease condition or disorder, wherein a beneficial effect may be evident by the modulation of the signal transduction associated with the 7TM-receptor. For example, the treatment may be of diseases that are caused by over-activity or under-activity of 7TM receptor. Examples of such diseases are: hypertension, stroke, heart failure, neurodegenerative diseases (including Alzheimer's disease), renal disease, psychiatric disease, cancer, asthma, diabetes and immune disorders.

Another example of beneficial therapeutic outcome may be in conditions where the activity of the 7TM receptor is normal, but nevertheless change of the signal transduction may improve the condition.

Based on methods disclosed herein, compounds can be designed in the future to modulate the activity of 7TM receptor whose unique region has been sequenced or will be sequenced in the future and whose cellular function is known. As a consequence, compounds can be designed to affect (increase or decrease) those cellular functions. It is possible that future research will reveal that certain disease conditions, whose underlying causes are presently unknown, are brought about by the overactivity or underactivity of cellular functions controlled by these 7TM receptor. These diseases can be treated by administering compounds comprising sequences obtained from the unique region or variants of the over- or under-active receptor. Compounds can be identified by methods disclosed above.

A "therapeutically effective amount" is the quantity of the compound which results in a "therapeutically beneficial effect" as a result of the treatment compared with a typical clinical outcome in the absence of the treatment.

A "therapeutically beneficial effect" results in the individual with the disease experiencing fewer symptoms or complications of the disease, including a longer life expectancy, as a result of the treatment.

The term "treatment" in the context of the invention includes: cure of the disease or condition, prevention of the disease before it occurs, or prevention of deterioration of the disease, as well as decrease in the severity of at least one undesired manifestation of the disease.

The amount of compounds of the invention administered to the individual will depend on the type and severity of the disease and on the characteristics of the individual, such as general health, age, sex, body weight and tolerance to drugs as well as on the mode of administration. The skilled artisan will be able to determine appropriate dosages depending on these and other factors. Typically, a therapeutically effective amount of the compound can range from about 1 mg per day to about 1000 mg per day for an adult. Preferably, the dosage ranges from about 1 mg per day to about 100 mg per day.

It should be appreciated that for the purpose of modulation, one should choose a compound comprising sequences derived from the same member of the 7TM receptor known (for example, in literature or from clinical information) to be involved in the specific disease, disorder or condition to be treated, or sequences derived from members of the same 7TM receptor family.

It should be appreciated that some of the compounds comprising the sequences of (b1) to (b6) above, are not active in modulating signal transduction associated by the 7TM receptor, and the selection of the compounds which are active in the above modulation should be done according to the method as indicated above.

Preferably, the determination of the sequence to be included in the candidate compound for modulating 7TM receptor-associated signal transduction should be carried out with the following steps:

(a) determining which specific 7TM receptor-associated signal transduction is to be modulated and determining the sequence of the specific 7TM receptor from a database of amino acid sequences;

(b) determining the unique region of the 7TM receptor by aligning the sequence of the $2^{nd}$ intracellular loop of rhodopsin of the 7TM receptor determined in (i) with the sequence, and determining the sequence of the specific 7TM receptor corresponding to positions 142-150 of rhodopsin ("unique region");

(c) determining a continuous stretch of at least 5 amino acids of any of the unique regions above that is shorter than the length of the full unique region and modulates the 7TM receptor-associated signal transduction, by synthesizing a plurality of subsequences (optionally partially overlapping subsequences) of 5-9 aa obtained from the unique region; testing those subsequences in a test assay for determining signal transduction associated with the 7TM receptor, and selecting those subsequences that modulated said signal transduction associated with the 7TM receptor;

(d) determining in the sequences of (b) or in the sequences selected in (c) above, essential and non-essential amino acids by: preparing a plurality of modified sequences wherein in each sequence a single and different amino acid of the native sequence has been replaced with a test amino acid (preferably with Ala) to produce modified sequences; testing those modified sequences in a test assay for determining signal transduction associated with the 7TM receptor; those amino acids which when replaced, caused a statistically significant change in signal transduction associated with the 7TM receptor being non-essential amino acids;

(e) preparing a plurality of compounds comprising sequences selected from:
  (1) the sequences of (b);
  (2) the sequences selected in (c);
  (3) the sequences of (b) or the selected sequence of (c), wherein at least one of the essential amino acids has been replaced by a conservatively substituted naturally or non-naturally occurring amino acid, or a conservative peptidomimetic organic moiety and/or the sequences of (b) or the selected sequence obtained in (c), wherein at least one of the non-essential amino acids has been deleted, or substituted (conservatively or non-conservatively) by naturally or non-naturally occurring amino acids or a peptidomimetic, or the sequences of (b) or (c) where at least one of the amino acids have been chemically modified;
  (4) the sequences of (1) to (3) in a reverse order,
  (5) the sequence of 4 wherein all the amino acids have been replaced by their D-counterpart residues;
  (6) sequences wherein at least one of the peptidic backbones has been altered to a non-naturally occurring peptidic backbone;

said compounds of (e) being candidate compounds for modulating 7TM receptor-associated signal transduction.

Conceptually, the first step is deciding which specific 7TM receptor is involved in the signal transduction which is to be modulated, for example by carrying out a literature search, and determining which 7TM receptor is known to be involved in the relevant pathway. The sequence of that 7TM receptor is the one used to determine the unique region sequence.

Once this specific 7TM receptor is chosen, its sequence can be determined from amino acid sequence databases and it is possible to locate the above unique region, simply by aligning the sequence of the $2^{nd}$ intracellular loop of the specific 7TM receptor chosen, as present in the database, with the $2^{nd}$ intracellular loop of rhodopsin. It is of course desirable to find shorter subsequence of at least 5 continuous amino acids present within this full unique region, and use these shorter sequences in the candidate compound of the invention.

Finding these short subsequences is a routine procedure, which can be achieved by several possible manners, such as by synthesizing subsequences of 5-9 aa having partially overlapping, or adjacent sequences, and optionally optimizing the chosen sequence (if rather longer sequences such as, for example, 8-9 aa are used) by sequentially deleting from one or both of its terminal amino acids until the optimal shorter sequence. The sequence chosen is not necessarily the shortest, but the best wherein a combination of best activity and shortest sequences are both taken into consideration.

After obtaining shorter subsequence, which still has signal-transduction modulating properties, it is necessary to find which amino acids, either in the sequence of the full region, but preferably in the sequence of the shorter subsequence, are essential (crucial for the modulating activity) and which are non-essential. This can be done by routine procedure, wherein a plurality of sequences are prepared, wherein in each sequence a single (and different) amino acid has been replaced, as compared to the native sequence by a "test amino acid"—usually the amino acid residue Alanine (a procedure known as: "Ala-scan"). Each of the plurality of sequences is again tested for its signal transduction modulating activities. Amino acids which when replaced cause lost, or substantial decrease (statistically significant change) in the modulating activity of the full sequence are considered as "essential amino acids" Identification of such essential amino asides may be carried out by other SAR techniques such as by site-directed mutagenesis or "omission scan". Amino acids which when replaced, or omitted, do not caused a statistically significant change of modulating activity of the sequence are referred to as "non-essential" amino acids.

Finally, as a last step, a plurality of sequences is prepared which may comprise either the full native sequence of the unique region, short subsequence of at least 5 (at least 6, 7, 8 or 9, amino acids as appearing in the unique region, (or the shorter subsequence), sequences wherein at least one essential amino acid has been replaced by conservative substitution by a naturally, non-naturally occurring amino acid or by a peptidomimetic organic moiety; and/or an amino acid sequence wherein at least one amino acid (present in a non-essential position) has been deleted, or an amino acid in a non-essential position has been replaced by conservative or non-conservative substitution by a naturally occurring, non-naturally occurring, or organic peptidomimetic moiety, and of at least one of any of the above has been chemically modified.

For example, 1, 2, 3 or 4, amino acids, both essential and non-essential may be replaced (both by conservative or non-conservative substitution) in the sequence used in a molecule of the invention as compared with the native sequence present in the unique region. The total of replacements should be of no more than 40% of the amino acids, 30% of the amino acid to 20% of the amino acid, or 10% of the amino acid. Preferably, in a short sequence of 10 amino acids there are 3 preferably 2, most preferably 1 non-conservative replacement and 4 preferably 3, more preferably 2, still more preferably 1 conservative replacements so long as the total number of replacements (conservative or non-conservative) in a 9 aa sequence is no more than 4. In longer sequences more replacements can be tolerated and in shorter sequences less replacements are possible.

A notable exception to the above is the use of retro-inverso amino acids (in reverse order as compared to the native sequence), where when the peptide is in the reversed order, all of its amino acids are replaced with their D-counterparts as defined above.

When preparing the compounds, it is possible to proceed by one of two strategies: by one strategy it is possible to test (for 7TM receptor-associated signal transduction modulating activities) a full compound—i.e. a molecule comprising both a candidate sequence, and for example, non-amino acid moieties such as hydrophobic moieties present in one of its terminals. This strategy is generally used where the test assay is carried out intact cells or in-vivo where the issue of penetration through membranes, addressed by addition of a hydrophobic moiety, is crucial.

Alternatively, it is possible to first optimize the sequence alone preferably by testing it in a cell-free system) so as to first find the best unique region sequence variant, or shortest unique region subsequence possible, and then add to the chosen sequence other moieties, such as hydrophobic moieties, etc. to improve other properties of the compound, such as penetration to cells, resistance to degradation, etc.

The present invention also concerns compounds for the modulation of signal transduction associated by a 7TM receptor obtained by the above methods.

The present invention also concerns a compound which has the property of modulation of signal transduction of a 7TM receptor comprising of at least one moiety for transport across cellular membranes, in association with a sequence selected from:

(1) a sequence comprising of from a minimum of 5 continuous amino acids of said unique region to a maximum of all the continuous amino acids of said unique region;

(2) a variant of the sequence of (1) wherein up to 40% of the amino acids of the sequence of (1) have been replaced with a naturally or non-naturally occurring amino acid or with a peptidomimetic organic moiety; and/or up to 40% of the amino acids have their side chains chemically modified, and/or up to 20% of the amino acids have been deleted, provided that at least 50% of the amino acids of (1) are maintained unaltered in the variant;

(3) a sequence of (1) or (2) wherein one or more of the amino acids is replaced by the corresponding D-amino acid;

(4) a sequence of any one of (1) to (3) wherein at least one peptidic backbone atom, or peptidic backbone bond has been altered to a modified peptidic backbone atom or a non-naturally occurring peptidic backbone bond, respectively;

(5) a sequence of any one of (1), (2), (3) or (4) in a reverse order; and (6) a combination of two or more of the sequences of (1), (2), (3), (4) or (5).

The term "moiety for transport across cellular membranes" refers to a chemical entity, or a composition of matter (comprising several entities) that causes the transport of members "associated" (see below) with it through phospholipdic membranes. One example of such moieties are linear, branched, cyclic, polycyclic or heterocyclic substituted or non-substituted hydrocarbons. Another example is fatty acids. Yet another example of such a moiety are short peptides that cause transport of molecules attached to them into the cell by, gradient derived, active or facilitated transport, as well as other non-peptidic moieties known to be transported through membranes such as glycosylated steroid derivatives, and the like. Other examples are moieties known to be internalized by receptors such as EGF, or transferrin agonists. The moiety of the compound may be a polymer, liposome or micelle containing, entrapping or incorporating therein the amino acid sequence. In such a case the compound is the polymer, liposome micelle etc impregnated with the amino acid sequence.

The term "in association" concerns covalent binding both of the type that is relatively permanent and of the type that can be cleaved by enzymes. The term may include entrapment (inside liposome), impregnation (in polymers), complexion through salt formation which can be dissociated in specific pH, or a specific ionic concentration. The term may also include other modes such as hydrophilic bonds, hydrogen bonds and electrostatic bonds.

The present invention further concerns pharmaceutical compositions comprising the above compounds as active ingredients. The pharmaceutical composition may contain one species of the compound of the invention or a combination of several species of the compounds of the invention.

The pharmaceutical compositions of the invention should be used for treatment of conditions or disorders wherein a therapeutic beneficial effect can be evident through the modulation of 7TM-receptor-associated signal transduction.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 1A and 1B show tables of active compounds comprising peptides derived from the unique region of the 7TM-receptors in accordance with the present invention. Peptides R002L103 (SEQ ID NO:4) and R002L106 (SEQ ID NO:5) are based on the peptide sequence SEQ ID NO:3 of EDG3 presented in FIG. 1A. The peptide sequence SEQ ID NO:6 from the $2^{nd}$ loop is presented in FIG. 1B along with peptides R013L101 (SEQ ID NO:7), R013L102 (SEQ ID NO:8), R013L103 (SEQ ID NO:9), R001L115 (SEQ ID NO:10), R001L116 (SEQ ID NO:11), K024H107 (SEQ ID NO:12), and K024H124 (SEQ ID NO:13).

FIG. 8D shows a synergistic effect of the compound of the invention R002L103 and FGF. FIG. 8A is the control and FIGS. 8B and 8C are FGF and R002L103 alone.

FIGS. 9A-9C show the results of neovascularization as a results of implantation of a pellet to the eye (FIG. 9A) in the presence of VEGF (FIG. 9B) and R002L103 (FIG. 9C) five days after administration.

DETAILED DESCRIPTION OF THE INVENTION

Figure 2B:
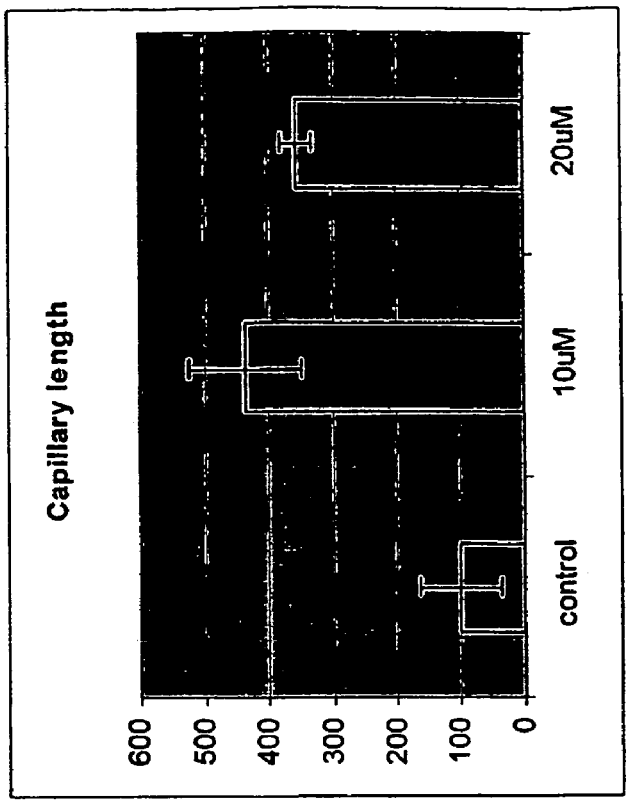
FIG. 2A shows a graph indicating capillary thickness and FIG. 2B shows a capillary length in the absence and presence of varying concentrations of the compound of the invention ROO2L103.

1. Addition of Non-Peptidic Groups to One or to Both of the Terminals of the A-Derived Sequences to Produce the Compound of the Invention Where the compound of the invention is a linear molecule, it is possible to place in any of its terminals various functional groups. The purpose of such a functional group may be for the improvement of the modulating activities of the 7TM receptor-associated signal transduction. The functional groups may also serve for the purpose of improving physiological properties of the compound not related directly to signal transduction modulation properties such as: improvement in stability, penetration, tissue localization, efficacy, decreased clearance, decreased toxicity, improved selectivity, improved resistance to repletion by cellular pumps, improved, or existence of penetration through barriers (blood-brain, gut), improved solubility and the like. For convenience sake the free N-terminal of one of the sequences contained in the compounds of the invention will be termed as the N-terminal of the compound, and the free C-terminal of the sequence will be considered as the C-terminal of the compound (these terms being used for convenience sake). Either the C-terminus or the N-terminus of the sequences, or both, can be linked to a carboxylic acid functional groups or an amine functional group, respectively.

Suitable functional groups are described in Green and Wuts, "*Protecting Groups in Organic Synthesis*" John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds these being an example for "a moiety for transport across cellular membranes".

These moieties can be cleaved in vivo, either by hydrolysis or enzymatically, inside the cell. (Ditter et al., *J. Pharm. Sci.* 57:783 (1968); Ditter et al., *J. Pharm. Sci* 57:828 (1968); Ditter et al., *J. Pharm. Sci.* 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988), Anderson et al., *Arch. Biochem. Biophys.* 239:538 (1985) and Singhal et al., *FASEB J.* 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a compound of the present invention is protected, preferably with a methyl, ethyl, benzyl or substituted benzyl ester, mote preferably as a benzyl ester.

In addition, a modified lysine residue can be added to the C-terminal of the compound to enhance biological activity. Examples of lysine modification include the addition of an aromatic substitute, such as benzoyl benzoic acid, dansyllysine various derivatives of benzoic acids (difluoro-, trifluromethy-, acetamido-, dimethyl-, dimethylamino-, methoxy-) or various derivatives of carboxylic acid (pyrazine-, thiophene-, pyridine-indole-, naphthalene-, biphenyl), or an aliphatic group, such as acyl, or a myristic or stearic acid, at the epsilon amino group of the lysine residue.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include —CH$_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoyl, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the molecule can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ nd R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH (ethyl), —N(ethyl)$_2$, —N(methyl)(ethyl), —NH(benzyl), —N(C1-C4 alkyl)(benzyl), —NH(phenyl), —N(C1-C4 alkyl)(phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

Preferably the compounds includes in the N-terminal a hydrocarbon having a length of $C_4$-$C_{12}$ preferably $C_6$-$C_{20}$, most preferably $C_{10}$-$C_{18}$. Example of hydrophobic moieties are: aceyl, stearyl, lauroyl, palmitoyl and acetyl, caproyl, farnezyl, geranyl, geranyl-geranyl etc.

2. Variants and Short Sequences

As one of the main mechanisms of action of the amino acid portion of the compounds of the invention is interruption of protein-protein interaction, it is clear that for such an interruption it is possible to use as a mimic one of several short sequences in the region. In addition, the mimic does not have to be identical to the sequence in the region since for the purpose of interruption similarity (of at least 50%) is required but a 100% identity is not a pre-requisite as will be shown below.

3. Finding a Shorter Subsequences of the A-Region

As indicated, the unique region from which the continuous stretch of at least five amino acids is chosen is identified by aligning the amino acid of the $2^{nd}$ intracellular loop of a specific 7TM receptor, involved in the signal transduction to be modulated, with the $2^{nd}$ intracellular loop unit of rhodopsin and determining the positions corresponding to 142-150 in rhodopsin (in the actual receptor the chosen the sequence may be longer or shorter than 9 aa, as typically, alignment programs can identify such missing or additional amino acids in the 7TM receptor as compared to the rhodopsin.)

A shorter subsequence of the unique region comprising a continuous stretch of at least five amino acid can be found by preparing a series of partially overlapping peptides each of 5-10 amino acids and each obtained by synthesizing a sequence that is one position removed from the previous sequence.

For example, if the unique region of a specific 7TM receptor is in position 142-150, (in this case 9 aa and it is to be desired to prepare 5 aa peptides), then the following, partially overlapping peptides are prepared, a peptide having the sequence 142-146, 143-147, . . . 146-150. The 7TM receptor-associated signal transduction activity is then determined in a test assay. The best 5-aa peptide is then chosen.

4. Identifying Essential and Non-Essential Amino Acids in the Subsequence Chosen Ala-Scan Once the shorter continuous stretch of at least 5 (at least 6, 7, 8 or 9) amino acids has been identified, as explained above, it is necessary to realize which of the amino acids in the stretch are essential (i.e. crucial for the signal transduction modulation) and which are non-essential. Without wishing to be bound by theory, in almost every native protein involved in interaction with other cellular components, some amino acids are involved with the interaction (essential amino acids) and some amino acids are not involved in the interaction (non-essential amino acids). A short peptide which is to mimic a region of the 7TM receptor protein behaves in the same way as the region when present in the full receptor: some amino acids actually interact with other interacting components (which may be for example G-protein) and other amino acids merely serve to spatially position the interacting amino acids, but do not participate in the interaction with the other cellular components.

Essential amino acids have to be maintained (i.e. be identical to those appearing in the native receptor), or replaced by conservative substitutions (see definition below) to obtain variants of the peptides. Non-essential amino acids can be deleted, or replaced by a spacer or by conservative or non-conservative substitutions.

Identification of essential vs. non-essential amino acids in the peptide can be achieved by preparing several peptides that have a shorter sequence (see 2 above) in which each position is sequentially replaced by the amino acid Ala ("Ala-Scan."). This allows to identify the amino acids which modulating activity is decreased by said replacement ("essential") and which are not decreased by said substitution ("non-essential") (Morrison et al., *Chemical Biology* 5:302-307, 2001). Another option for testing the importance of various peptides is by the use of site-directed mutagenesis.

5. Obtaining Variants

The sequence regions of the compound of the invention may be the native sequences obtained from the 7TM receptor preferably the shortest possible sequence from the unique region that has the highest activity), or alternatively variants of the native sequence obtained by deletion, (of non-essential amino acids) or substitution (only conservative substitutions in essential positions, both conservative and non-conservative of non-essential acids). As well as by chemical modifications of the side chains.

5.1 Deletions and Insertions

Deletions can occur in particular of the "non-essential amino acids". Additions may occur in particular at the N-terminal or the C-terminal of any of the amino acids of the sequence. Insertions should preferably be N-terminal or C-terminal to the sequence of (b1) to (b5) or between the several sequences linked to each other (b6). However other insertions or deletions are possible.

5.2 Replacements

The variants can be obtained by replacement (termed also in the text as "substitution") of any of the amino acids as present in the native 7TM receptor. As may be appreciated there are positions in the sequence that are more tolerant to substitutions than others, and in fact some substitutions may improve the activity of the native sequence. The determination of the positions may be realized using Ala-Scan, "omission scan" "site directed mutagenesis" as described above. Generally speaking the amino acids which were found to be "essential" should either be identical to the amino acids present in the native specific 7TM receptor or alternatively substituted by "conservative substitutions" (see below). The amino acids which were found to be "non-essential" might be identical to those in the native peptide, may be substituted by conservative or non-conservative substitutions, and may be deleted or replaced by a "spacers".

The term "naturally occurring amino acid" refers to a moiety found within a peptide and is represented by —NH—CHR—CO—, wherein R is the side chain of a naturally occurring amino acid.

The term "non-naturally occurring amino acid" (amino acid analog) is either a peptidomimetic and D-counterpart of a naturally occurring amino acid, or is a D or L residue having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. This term also refers to the D-amino acid counterpart of naturally occurring amino acids. Amino acid analogs are well-known in the art; a large number of these analogs are commercially available. Many times the use of non-naturally occurring amino acids in the peptide has the advantage that the peptide is more resistant to degradation.

The term "conservative substitution" in the context of the present invention refers to the replacement of an amino acid present in the native sequence in the specific 7TM receptor with a naturally or non-naturally occurring amino or a peptidomimetic having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid). However where the native amino acid to be replaced is charged, the conservative substitution according to the definition of the invention may be with a naturally occurring amino acid, a non-naturally occurring amino acid or a peptidomimetic moiety which are charged, or with non-charged (polar, hydrophobic) amino acids that have the same steric properties as the side-chains of the replaced amino acids. The purpose of such a procedure of maintaining the steric properties but decreasing the charge is to decrease the total charge of the compound.

For example in accordance with the invention the following substitutions are considered as conservative: replacement of arginine by cytroline; arginine by glutamine; aspartate by asparagine; glutamate by glutamine.

As the naturally occurring amino acids are grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid would have the same or a similar functional group in the side chain as the original amino acid.

The following are some non-limiting examples of groups of naturally occurring amino acids or of amino acid analogs are listed bellow. Replacement of one member in the group by another member of the group will be considered herein as conservative substitutions:

Group I includes leucine, isoleucine, valine, methionine, phenylalanine, serine, cysteine, threonine and modified amino acids having the following side chains: ethyl, n-butyl, —CH$_2$—CH$_2$OH, —CH$_2$—CH$_2$CH$_2$OH, —CH$_2$CHOHCH$_3$ and —CH$_2$SCH$_3$. Preferably Group I includes leucine, isoleucine, valine and methionine.

Group II includes glycine, alanine, valine, serine, cysteine, threonine and a modified amino acid having an ethyl side chain. Preferably Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester or glutamic or aspartic acid (e.g., methyl, ethyl, n-propyl iso-propyl, cyclohexyl, benzyl or substituted benzyl), glutamine; asparagine, CO—NH-alkylated glutamine or asparagine (e.g., methyl, ethyl, n-propyl and iso-propyl) and modified amino acids having the side chain —(CH$_2$)$_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, glutamine, asparagine, methyl aspartate, ethyl aspartate, benzyl aspartate and methyl glutamate, ethyl glutamate and benzyl glutamate.

Group V includes histidine, lysine, arginine, N-nitroarginine, β-cycloarginine, μ-hydroxyarginine, N-amidinocitruline and 2-amino-4-guanidinobutanoic acid, homologs of lysine, homologs of arginine and ornithine. Preferably, Group V includes histidine, lysine, arginine, and ornithine. A homolog of an amino acid includes from 1 to about 3 additional methylene units in the side chain.

Group VI includes serine, threonine, cysteine and modified amino acids having C1-C5 straight or branched alkyl side chains substituted with —OH or —SH. Preferably, Group VI includes serine, cysteine or threonine.

In this invention any cysteine in the original sequence or subsequence can be replaced by a homocysteine or other sulfhydryl-containing amino acid residue or analog. Such analogs include lysine or beta amino alanine, to which a cysteine residue is attached through the secondary amine yielding lysine-epsilon amino cysteine or alanine-beta amino cysteine, respectively.

The term "non-conservative substitutions" concerns replacement of the amino acid as present in the native 7TM receptor by another naturally or non-naturally occurring amino acid, having different electrochemical and/or steric properties, for example as determined by the fact the replacing amino acid is not in the same group as the replaced amino acid of the native 7TM receptor sequence. Those non-conservative substitutions which fall under the scope of the present invention are those which still constitute a compound having 7TM receptor-associated signal transduction modulating activities. Because D-amino acids have hydrogen at a position identical to the glycine hydrogen side-chain, D-amino acids or their analogs can often be substituted for glycine residues, and are a preferred non-conservative substitution A "non-conservative substitution" is a substitution in which the substituting amino acid (naturally occurring or modified) has significantly different size, configuration and/or electronic properties compared with the amino acid being substituted. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid.

Alternatively, a functional group may be added to the side chain, deleted from the side chain or exchanged with another functional group. Examples of non-conservative substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties from the functional group of the amino acid being substituted. Examples of such modifications include tryptophan for glycine, lysine for aspartic acid and —(CH$_2$)$_4$COOH for the side chain of serine. These examples are not meant to be limiting.

As indicated above the non-conservative substitutions should be of the "non-essential" amino acids.

"Peptidomimetic organic moiety" can be substituted for amino acid residues in the compounds of this invention both as conservative and as non-conservative substitutions. These peptidomimetic organic moieties either replace amino acid residues of essential and non-essential amino acids or act as spacer groups within the peptides in lieu of deleted amino acids (of non-essential amino acids). The peptidomimetic organic moieties often have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the compounds retain the modulating activity as compared to compounds constituting sequence regions identical to those appearing in the native 7TM receptor.

Peptidomimetics are often used to inhibit degradation of the peptides by enzymatic or other degradative processes. The peptidomimetics can be produced by organic synthetic techniques. Examples of suitable peptidomimetics include D amino acids of the corresponding L amino acids, tetrazol (Zabrocki et al., *J. Am. Chem. Soc.* 110:5875-5880 (1988)); isosteres of amide bonds (Jones et al., Tetrahedron Lett. 29: 3853-3856 (1988));

LL-3-amino-2-propenidone-6-carboxylic acid (LL-Acp) (Kemp et al., *J. Org. Chem.* 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., *J. Org. Chem.* 54:109-115 (1987). Other suitable peptidomimetics are shown in Nagai and Sato, Tetrahedron Lett. 26:647-650 (1985); Di Maio et al., *J. Chem. Soc. Perkin Trans.,* 1687 (1985); Kahn et al., Tetrahedron Lett. 30:2317 (1989); Olson et al., *J. Am. Chem. Soc.* 112:323-333 (1990); Garvey et al., *J. Org. Chem.* 56:436 (1990). Further suitable peptidomimetics include hydroxy-1,2,3,4-tetrahydroisoquinoline-3-carboxylate (Miyake et al., *J. Takeda Res. Labs* 43:53-76 (1989)); 1,2,3,4-tetrahydro-isoquinoline-3-carboxylate (Kazmierski et al., *J. Am. Chem. Soc.* 133:2275-2283 (1991)); histidine isoquinolone carboxylic acid (HIC) (Zechel et al., *Int. J. Pep. Protein Res.* 43 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)).

5.3 Chemical Modifications

In the present invention the side chains of the amino acid residue appearing in the native sequence may be chemically modified when the individual residue is still an isolated moiety, and that the chemically modified amino acid residue may be used as a building block, in the process of synthesis of the molecule, i.e. during elongation of the amino acid chain. Another alternative is chemical modification of an amino acid when it is present in the molecule or sequence ("in situ" modification).

The amino acid of any of the sequence regions of the molecule can be chemically modified by carboxymethylation, carboxyacrylation, acylation, phosphorylation, iodination, glycosylation or fatty acylation. Ether bonds can be used to join the serine or threonine hydroxyl to the hydroxyl of a sugar. Amide bonds can be used to join the glutamate or aspartate carboxyl groups to an amino group on a sugar (Garg and Jeanloz, Advances in *Carbohydrate Chemistry and Biochemistry*, Vol. 43, Academic Press (1985); Kunz, *Ang. Chem. Int.* Ed. English 26:294-308 (1987)). Acetal and ketal bonds can also be formed between amino acids and carbohydrates. Fatty acid acyl derivatives can be made, for example, by free amino group (e.g., lysine) acylation (Toth et al., Peptides: *Chemistry, Structure and Biology*, Rivier and Marshal, eds., ESCOM Publ., Leiden, 1078-1079 (1990)). Additions of various groups to Lysine residue are also disclosed above.

5.4 Cyclization of the Molecule

The present invention also includes cyclic compounds which are cyclic molecules.

A "cyclic molecule" refers, in one instance, to a compound of the invention in which a ring is formed by the formation of a peptide bond between the nitrogen atom at the N-terminus and the carbonyl carbon at the C-terminus.

"Cyclized" also refers to the forming of a ring by a covalent bond between the nitrogen at the N-terminus of the compound and the side chain of a suitable amino acid in the sequence present therein, preferably the side chain of the C-terminal amino acid. For example, an amide can be formed between the nitrogen atom at the N-terminus and the carbonyl carbon in the side chain of an aspartic acid or a glutamic acid. Alternatively, the compound can be cyclized by forming a covalent bond between the carbonyl at the C-terminus of the compound and the side chain of a suitable amino acid in the sequence contained therein, preferably the side chain of the N-terminal amino acid. For example, an amide can be formed between the carbonyl carbon at the C-terminus and the amino nitrogen atom in the side chain of a lysine or an ornithine. Additionally, the compound can be cyclized by forming an ester between the carbonyl carbon at the C-terminus and the hydroxyl oxygen atom in the side chain of a serine or a threonine.

"Cyclized" also refers to forming a ring by a covalent bond between the side chains of two suitable amino acids in the sequence present in the compound, preferably the side chains of the two terminal amino acids. For example, a disulfide can be formed between the sulfur atoms in the side chains of two cysteines. Alternatively, an ester can be formed between the carbonyl carbon in the side chain of, for example, a glutamic acid or an aspartic acid, and the oxygen atom in the side chain of, for example, a serine or a threonine. An amide can be formed between the carbonyl carbon in the side chain of, for example, a glutamic acid or an aspartic acid, and the amino nitrogen in the side chain of, for example, a lysine or an ornithine.

In addition, a compound can be cyclized with a linking group between the two termini, between one terminus and the side chain of an amino acid in the compound, or between the side chains to two amino acids in the peptide or peptide derivative. Suitable linking groups are disclosed in Lobl et al., WO 92/00995 and Chiang et al., WO 94/15958, the teachings of which are incorporated into this application by reference.

6. Pharmaceutical Compositions and Therapeutic Methods of Treatment

The compound of the present invention can be used as an active ingredient (together with a pharmaceutically acceptable carrier) to produce a pharmaceutical composition. The pharmaceutical composition may comprise one, or a mixture of two or more of the compounds of the invention in an acceptable carrier. A combination of two or more different compounds is desirable for example, where a disease or condition requires the modulation of two or more 7TM receptor-associated signaling (either in the same or in different pathways) In such a case the composition may comprise two different compounds, each comprising a sequence derived from the unique region of a different 7TM receptor.

The pharmaceutical composition should be used for the treatment of a disease disorder or pathological condition wherein a therapeutically beneficial effect may be evident due to modulation (increase or decrease) of at least one 7TM receptor-associated signal transduction. Typically those are diseases in which one of their manifestations (a manifestation that may be the cause or the result of the disease) is non-normal 7TM receptor-associated signaling transduction, or diseases or conditions where, although the activity is normal, a therapeutic beneficial effect may nonetheless be evident by modulating (increasing or decreasing) the activity of the 7TM receptor-associated signal transduction.

The compounds of the present invention can be administered parenterally. Parenteral administration can include, for example, systemic administration, such as by intramuscular, intravenous, subcutaneous, or intraperitoneal injection. Compounds which resist proteolysis can be administered orally, for example, in capsules, suspensions or tablets. The compound can also be administered by inhalation or insufflations or via a nasal spray.

The compound can be administered to the individual in conjunction with an acceptable pharmaceutical carrier as part of a pharmaceutical composition for treating the diseases discussed above. Suitable pharmaceutical carriers may contain inert ingredients which do not interact with the compounds. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., *Controlled Release of Biological Active Agents*, John Wiley and Sons, 1986). The formation may be also resources for administration to bone, or in the form of salve, solution, ointment, etc. for topical administration.

7. Preparation of the Compounds

Peptide sequences for producing any of the sequence of the compounds of the invention may be synthesized by solid phase peptide synthesis (e.g., t-BOC or F-MOC) method, by solution phase synthesis, or by other suitable techniques including combinations of the foregoing methods. The t-BOC and F-MOC methods, which are established and widely used, are described in Aarifield, *J. Am. Chem. Soc.*, 88:2149 (1963); Meienhofer, Hormonal Proteins and Peptides, C. H. Li, Ed., Academic Press, 1983, pp. 48-267; and Barany and Aarifield, in The Peptides, E. Gross and J. Meienhofer, Eds., Academic Press, New York, 1980, pp. 3-285. Methods of solid phase peptide synthesis are described in Aarifield, R. B., *Science*, 232:341 (1986); Carpino, L. A. and Han, G. Y., *J. Org. Chem.*, 37:3404 (1972); and Gauspohl, H. et al., *Synthesis* 5:315 (1992)). The teachings of these references are incorporated herein by reference.

As indicated above the compounds of the invention may be prepared utilizing various peptidic cyclizing techniques. Methods of cyclizing compounds having peptide sequences are described, for example, in Lobl et al., WO 92/00995, the teachings of which are incorporated herein by reference. Cyclized molecules can be prepared by protecting the side chains of the two amino acids to be used in the ring closure with groups that can be selectively removed while all other side-chain protecting groups remain intact. Selective deprotection is best achieved by using orthogonal side-chain protecting groups such as allyl (OAl) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAl and Aloc are easily removed by Pd and Acm is easily removed by iodine treatment.

Other modes of cyclization (beyond N- to C-terminal cyclization) may include: N- to backbone cyclization, C- to backbone cyclization, N- to side chain cyclization, C- to side chain cyclization, backbone to side chain cyclization, backbone to backbone cyclization and side chain to side chain cyclization.

8. Determination of 7TM Receptor-Associated Signal Transduction Modulating Activity It should be appreciated that some of the compounds that comprise sequences (b1)-(b6) above have modulating activities of the signal transduction associated with the 7TM receptor while some do not. Some of the conservative substitutions in the essential positions may diminish the modulating activities altogether, while other such conservative substitution in the essential positions may improve these modulating activities. The same is true also for deletions, substitutions (both conservative and non-conservative) in non-essential positions, as well as to chemical modifications (in any position) or insertions. In addition the type and size of the non-amino acid portion of the compounds, such as a hydrophobic moiety in one of its terminals may diminish or increase the modulation of the signal transduction. Those compounds which fall under the scope of the present invention are those that have signal transduction modulating activities, which activities that can be determined for example by using one of the assays stipulated below.

8.1 Cellular Assay

It can be readily determined whether a compound modulates the signal transduction associated with a 7TM receptor by incubating the compound with cells which have one or more cellular activities controlled by the specific signal transduction associated with the receptor. Examples of these cellular activities include cell proliferation, cell differentiation, cell morphology, cell survival or apoptosis, cell response to external stimuli, gene expression, lipid metabolism, glycogen or glucose metabolism, mitosis, GTP or second messenger production and the like. The cells are incubated with the candidate compound to produce a test mixture under conditions suitable for assessing the level of the signal transduction associated with the 7TM receptor. The activity of the signal transduction is assessed and compared with a suitable control, e.g., the activity of the same cells incubated under the same conditions in the absence of the candidate compound (or in the presence of a control compound). A greater or lesser activity of the signal transduction in the test mixture compared with the control indicates that the candidate compound modulated the signal transduction associated with the 7TM receptor.

Suitable cells for the assay include normal cells which express the 7TM receptor, cells which have been genetically engineered to express a 7TM receptor, malignant cells expressing a 7TM receptor or immortalized cells that express the 7TM receptor.

Conditions suitable for assessing activity include conditions suitable for assessing a cellular activity or function under control of the signal transduction associated with the 7TM receptor signal transduction pathway. Generally, a cellular activity or function can be assessed when the cells are exposed to conditions suitable for cell growth, including a suitable temperature (for example, between about 30° C. to about 42° C.) and the presence of the suitable concentrations of nutrients in the medium (e.g., amino acids, vitamins, growth factors or of specific activators such as cytokines, hormones and the like).

Generally, the level of the signal transduction associated with the 7TM receptor in the test mixture is assessed by making a quantitative measure of the cellular activity which the signaling controls. The cellular activity can be, for example, cell proliferation, GTP production, etc. Signal transduction associated with the 7TM receptor is assessed by measuring cellular proliferation, for example, by comparing the number of cells present after a given period of time with the number of cells originally present.

9. Using the Compounds of the Invention to Identify Ligands

The unique region within 7TM receptor plays a key role in the 7TM receptor associated signal transduction. The compound comprising the unique region peptides of the present invention can also be used to identify ligands which interact with the unique regions of a specific 7TM receptor and thus can modulate the 7TM receptor-associated signal transduction. For example, an affinity column can be prepared to which a specific unique region peptide is covalently attached, directly or via a linker. This column, in turn, can be utilized for the isolation and identification of specific ligands which bind the unique region peptide and which will also likely bind the receptor from which the unique region peptide was derived. The ligand can then be eluted from the column, characterized and tested for its ability to modulate receptor function. The peptides may also be used as a research tool for identifying the components with which the 7TM receptor interacts.

Example 1

Preparation of Compounds of the Invention

The novel compounds of this invention can be synthesized utilizing a 430A Peptide Synthesizer from Applied Biosystems using F-Moc technology according to manufacturer's protocols. Other suitable methodologies for preparing sequences are known to person skilled in the art. See e.g., Aarifield, R. B., *Science*, 232: 341 (1986); Carpino, L. A., Han, G. Y., *J. Org. Chem.*, 37: 3404 (1972); Gauspohl, H., et al., *Synthesis*, 5: 315 (1992)), the teachings of which are incorporated herein by reference.

Rink Amide Resin [4(2',4' Dimethoxyphenyl-FMOC amino methyl)phenoxy resin] was used for the synthesis of C-amidated peptides. The alpha-amino group of the amino acid was protected by an FMOC group, which was removed at the beginning of each cycle by a weak base, 20% piperidine in N-methylpyrrolidone (NMP). After deprotection, the resin was washed with NMP to remove the piperidine. In situ activation of the amino acid derivative was performed by the FASTMOC Chemistry using HBTU (2(1-benzotriazolyl-1-yl)-1,1,3,3-tetramethyluronium) dissolved in HOBt (1-hydroxybenzotriazole) and DMF (dimethylformamide). The amino acid was dissolved in this solution with additional NMP. DIEA (diisopropylethylamine) was added to initiate activation. Alternatively, the activation method of DCC (dicyclohexylcarbodiimide) and HOBt was utilized to form an HOBt active ester. Coupling was performed in NMP. Following acetylation of the N-terminus (optional), TFA (trifluoroacetic acid) cleavage procedure of the peptide from the resin and the side chain protecting groups was applied using 0.75 g crystalline phenol; 0.25 ml EDT (1,2-ethandithiol); 0.5 ml thioanisole; 0.5 ml D.I. $H_2O$; 10 ml TFA.

Example 2

Determination of Angiogenesis Modulating Properties

In accordance with the angiogenesis aspect it should be appreciated that some of the compounds that comprise sequences (a)-(i) above have better properties in modulating angiogenesis than others. Some of the conservative substitutions in the essential positions may diminish the angiogenesis modulating properties, while other such conservative substitution in the essential positions may improve these properties. The same is true also for deletions, substitutions (both conservative and non-conservative) in non-essential positions, as well as to chemical modifications of the side chains (in any position) or insertions. In addition the type and size of the non-amino acid portion of the compounds, such as a hydrophobic moiety in one of its terminals, may diminish or increase the angiogenesis modulating properties. The angiogenesis modulating properties may be determined by using one of the assays below.

2.1 Cellular Assay

An indication on the angiogenesis modulating properties may be by the determination of the change of the proliferation of endothelial cells or Smooth Muscle Cells (SMC) (for example using the methylene blue technique). However lack of effect on the proliferation is not conclusive as regards lack of effect on the angiogenesis, as many times angiogenesis is changed even without change in the proliferation of the endothelial cells for example by interruption/inhibition of the endothelial and/or smooth muscle cell-cell interactions and their arrangement in regular structures.

The activity of the candidate compound is assessed and compared with a suitable control, e.g., the proliferation of the same cells incubated under the same conditions in the absence of the candidate compound (or in the presence of a control compound). A greater or lesser proliferation as compared with the control indicates that the candidate compound modulates endothelial and/or smooth muscle cell proliferation alluding to a possible effect (that has to be verified) on angiogenesis.

2.2 Tissue or In Vivo Assays

The following are suitable in vivo or ex vivo modes for angiogenesis:
(1) Aortic ring—where sprouting of newly formed blood vessels is tested whole mounts of aortic rings obtained from rats (see below)
(2) Eye assay—where formation of new blood vessels in the cornea of the animal as a response to an FGF-implanted pellet is determined (see below).
(3) Sponge assay—where infiltration of new blood vessels into a sponge implanted s.c. in an experimental animal is determined (see below)

(4) Regression of pre-formed vasculature in tumors (Benjamin L. E. and Kesshet E. *PNAS*, 94, 8761-8766, (1997)).

(5) Re-establishment of circulation in dissected vessels in the limbs of experimental animals.

Experimental Procedures:

1. Aortic Ring-Assay:

The modification of previously described assay (Nicosia, R. F. and Ottinetti, A. "Growth of microvessels in serum-free matrix culture of rat aorta." *Lab. Invest.* 63:115-122. 1990) for capillary growth ex vivo was used. The assay is based on the phenomenon of endothelial cells proliferation from freshly prepared aorta placed into collagen matrix gel, that finally formed new capillary system.

1.1 Collagen Extraction

Collagen solution was prepared by extraction from rat tendons (modification of the described assays—Strom, S. C. and Michalopoulos, G. "Collagen as a substrate for cell growth and differentiation." Methods Enzymol. 82:544-55. 1982). For this purpose, rat tails were taken from SABRA rats that were sacrificed in the lab during the different experiments. The tails are stored frozen at −20° C. until the day of extraction. About 15 tails are used to produce 1 liter of collagen.

Rat tails were thawed and a section of skin from proximal end of each tail was removed using bone clippers. Remaining skin was pulled away while keeping the tail intact to reveal the white tendons. Tails were washed with DDW. We used two pairs of artery forceps to dissect out tail tendons. Starting from the tip of the tail, the tail was clamped at its end with the artery forceps and using the other clamp approximately 2-3 cm away from another pair, the tail was bended until the vertebrae break and tendons come loose from the remaining of the tail. This procedure was repeated several times toward the distal end of the tail. Tendons were cut, washed twice with PBS and placed into Petri dish with 70% Ethanol for sterilization and dehydration. Remaining blood vessels were removed before sterilization. Petri dish with tendons is placed under UV and ethanol is evaporated during overnight incubation.

Then collagen fibers were weighted and solubilized in sterile 0.1% solution of Acetic Acid in DDW* (1-2 gr per 0.5 liter). Solution was stirred slowly at 4° C. during 48 h. Undissolved tendons are then discarded by centrifugation (16,000-20,000 g, 30'). Collagen Stock solution is stored at −20° C. Prior to storage, the collagen was assayed using the polymerization reaction described below. The polymer was examined for both viscosity and cleanliness from remaining tendon particles. Too viscous collagen was diluted in acetic acid. Too "dirty" is being centrifuged again, at higher speed.

The collagen matrix gel was obtained by simultaneously raising of pH and ionic strength of collagen solution (Elsdale and Bard, 1972). Working solution for this purpose was prepared by the following proportion:

Collagen Stock Solution—7 Parts,

MEM×10 (Minimum Essential Medium Eagle concentrated×10 (obtained from Beit Haemec, cat. 01-025-5A).—1 part, Na Bicarbonate 0.15M solution—2 parts.

1.2 Experimental Animals.

The experiments were carried out on two lines of animals—Sabra and Sprague-Dawley rats, males of 200-250 g-body weight (1-2 month old). Rats were acclimated to vivarium for 4-10 days before their use in study protocol. Each group (from 2 to 4) of the animals was housed in separate cage and fed food and water ad libitum.

1.3 Preparation of Aortic Rings.

Animals were sacrificed by decapitation after ether anesthesia Thoracic aortas were dissected and immediately transferred to a Petri dish with bio-mpm-1. The fibroadipose tissue and small vessels around aorta was carefully removed under a dissecting microscope, 1 mm-long aortic rings were sectioned and extensively (2-3 times) rinsed in bio-mpm-1 containing antibiotics (% cat.) (Nicosia and Ottinetti, 1990).

1.4 Embedding of Aortic Rings.

The collagen matrix gel solution (see above) was added to 24-well plate (0.4 ml to each well) and collagen polymerization was allowed for 15 min at 37° C. The aorta rings were transferred to the collagen gel solution (in order to glue them to the bottom layer of the gel) and then placed to the center of each well. In mice, 3 rings are embedded in the same well. After 15 min incubation of the plates at 37° C. another 0.4 ml of the collagen solution was carefully added on the top of the ring. After the gel is formed 0.4 ml of Serum-Free Endothelial Growth Medium (Rhenium, cat. 17601-030) or bio-mpm-1 (Beit Haemeq cat. 05-060-1) was added to each well. Rings were incubated in 37° c. and 10% $CO_2$. Medium is replaced every 2-3 days.

1.5 Addition of Compounds

Compound of the invention were added next day after collagen gel formation in concentration 10-20 uM. compounds were dissolved for 10 mM stock in 100% DMSO. Dilution in 0.1% BSA in PBS to 400 uM stock were done for each AR experiment de novo. The compounds were re-added to AR during each medium changing till well developed capillary system in control or experimental wells.

1.6 Experimental Treatment

Fixation.

Fixation was carried out by adding of Buffered Formalin 4% (was obtained from BioLab, cat. 66554) 1.5 ml in each well. An hour later solution was changed to fresh Formalin in order to better fixation (overnight).

Staining.

We used Crystal Violett (Gencian Violett) 0.02% in Ethanol Abs. as staining solution (1 ml for each well overnight at room temperature). After staining, wells were washed massively with 0.02% Sodium Azide water solution during two or three days till transparent matrix.

1.7 Analysis of Results

Digital pictures were analyzed using ImagePro™ software. The total capillary length of at least 6 AR was measured. Dividing the total capillary length to AD diameter normalized the data.

2. Eye Assay

The modification of the assay previously described in "A model of angiogenesis in the mouse cornea" B. M. Kenyon, E. E. Voest, C. C. Chen, E. Flynn J. Folkman and R. J. D'Amato Investigative Ophthalmology & Visual Science, July 1996, Vol. 37, No. 8 1625-1632 was used. The assay is based on the phenomena of formation of new blood vessels in the cornea of mice in response to the implantation in the cornea of a pellet impregnated with FGF.

2.1 FGF Pellets Preparation.

1. Weight Out: −120 mg hydron into sterile screwcup
   −10 mg sterile sucralfate into Eppendorf.

2. Add 1 ml 100% ethyl alcohol to hydron. Vortex till clear (few minutes).

3. Add 20 ng/20 µl bFGF to sucralfate-vortex, spidvac for 5 min (more if needed).

4. Add ~10 µl hydron solution to sucralfate pellet.

5. Mix with sterile spatula

6. Using spatula, remove mixture from tube and smear into nylon square (very quick).

7. Coat each side with hydron—light coat.

8. Stand it on dish to dry—glue the mesh with tape to the bottom and to the wall of the plate—pellets must stay in the air (using bacteriological 100 mm plates—less charged).

9. Dry till firm—30 min

10. Store at −20° C. till implantation procedure.

11. Pull trends releasing pellets.

12. Choose the pellets with the same size—the white pellets are the FGF containing, the transparent ones are hydron only.

2.2 Materials 1. bFGF—human recombinant
2. Sucralfate—sucrose octasulfate—aluminium complex Sigma cat. S-0652
3. Hydron—soluble poly-2-hydroxyethylmethacrylate cat.-97001
4. Mesh—Sefar America Kansas city, Mo. 64119-3120 Cat. 03-300/51, 40 inches wide Solution for FGF and Peptides (Solution S):
20 mM sodium citrate-1 mM EDTA
9% sucrose
pH 5.0

2.3 Peptide and Peptide+FGF Pellets Preparation.

1. To prepare—Hydron concentrated stock solution (120 mg/ml in ethanol Abs.)
Hydron diluted stock solution (60 mg/ml in ethanol Abs.) sucralfate stock solution (500 mg/ml in solution S sterile!).
10 mg peptide.

2. Add 30 µl of solution S to peptide (or 10 µl of solution S and 20 µl of FGF).

3. Add 20 µl of sucralfate stock solution—vortex, speedvac for 5 min (more if needed).

4. Add ~20 µl hydron diluted stock solution to sucralfate+ FGF+peptide pellet.

5. Mix with sterile spatula.

6. Using spatula, remove mixture from tube and smear into nylon square (very quick).

7. Coat each side with hydron concentrated solution—light coat.

8. Stand it on dish to dry—glue the mesh with tape to the bottom and to the wall of the plate—pellets must stay in the air (using bacteriological 100 mm plates—less charged).

9. Dry till firm—30 min

10. Store at −20° C. till implantation procedure.

11. Pull trends releasing pellets.

12. Choose the pellets with the same size—the white pellets are the FGF containing, the transparent ones are hydron only.

2.4 Implantation Procedure

Mice were anesthetized with Ketamin/Rompun Solution (for dosage and solutions preparation see standard anesthetic procedure). The eye is topically anesthetized with Localin (Benoxynate HCl 0.4%, Dr. Fisher, Pharmaceutical Labs, P.O.B. 39071, Tel-Aviv 61390). Using a binocular microscope, a central intrastromal linear keratotomy is performed with a surgical blade parallel to the insertion of the lateral rectus muscle. Approximate length of the cut is 0.5-0.6 mm length. The globe is proptosed with a forceps. A lamellar micropocket is dissected toward the temporal limbus using the modified von Graefe knife 2×30 mm. All following procedures must be done without proptosis. A pellet is placed on the corneal surface in the base of the pocket and advanced to the temporal end of the pocket with one arm of the forceps. The distance between pellet and limbal vessel is measured. For FGF containing pellets, the pocket must be extended within 1 mm of the limbus. Antibiotic and antimycotic ointment are applied to the operated eye to prevent infection and additional irritation of the cornea.

2.5 Experimental Procedure

Measurements were done at $5^{th}$ and $7^{th}$ days after implantation. In the case of high stimulation inspections were done twice a week till full degradation. The maximum vessel length of neovascularization zone, extending from the limbal vessel toward the pellet was measured. The econtiguous circumferential zone of neovascularization was measured as clock hours (where 30° are equals 1 clock hour.)

3. Air Sac Model ('Sponge Assay")

The modification of previously described assays (J. Lichtenberg, C. A. Hancen et al. was used "The rat subcutaneous Air Sac Model: a new and simple method for in vivo screening of angiogenesis." *Pharmacology and Toxicology* 1997. 81:280-284, A. P. Lage and S. P. Andrade "Assessment of angiogenesis and tumor growth in conscious mice by a fluorometric method.").

3.1 Experimental Animals

The experiments were done at BalbC mice, males of 6-7 week age. Mice were acclimated to vivarium for four days before their use in study protocol. Each group (from 8 to 10) of the animals was housed in separate cage and fed food and water ad libitum. The animals were observed daily for clinical signs and body weights were recorded twice weekly.

3.2 Implant

Sponge pieces was used for subcutaneous implantation. The sponges were sterilized by autoclaving at 121° C. for 15 min. The cellulose sponge SpontexR (manufactured by Spontex S.A., Beauvais, France) has previously been used in an in vivo experiments for the study of cartilage degradation (Bishop et al. "A novel model of cartilage segregation." *J. Pharmacol. Toxicol. Meth.* 1993, 30:19-25).

3.3 Air Sac Formation.

4-5 ml of air were introduced dorsally by subcutaneous injection using a 27 gauge needle to produce an air sac located in the middle of the back. The air sacs were re-inflated every forth day. The wall of the air sac became progressively thicker with time, and after approximately 10 days a sufficient lining of cells had been established. The implantation of the sponge was made not sooner than 10 days after induction of air sac.

3.4 Implantation Technique.

All mice received intraperitoneal injection of anesthetic solution 0.1 ml per animal before implantation. Solution was prepared at the day of the treatment as followed: 0.85 ml of Ketamin 100 mg/ml (was obtained from Fort Dodge, NDS 0856-2013-01), 0.15 ml of Rampun 2% (Xylazine HCl 10%, obtained from "Bar-Ilan", B-8049), 1 ml PBS. After injection animals was shaved, marked and separate to the groups.

Each animal was placed on its abdomen and the skin of the back was washed with Ethanol 70%. A 0.5-0.7 cm incision was made through the skin covering the air sac. Blunt dissection was used to open a 1 cm deep cavity towards the cranial base of the air sac by careful separation of the skin from the membrane. A sponge implant (0.5×0.5×0.2 cm) was carefully inserted to the pocket on the membrane away from the incision. The incision was closed by 2-3 sutures using DexonR 3-0.

3.5 Angiogenic Response.

The animals were sacrificed by ether aspiration. The overlying skin was carefully removed to expose the transparent membrane and not to rupture the air sac. The extent vascular proliferation was scored in situ. The subjective scoring was taken by following criteria:

0—transparent membrane without vascularization (blank membranes without implant).
1+—slight background vascularization.
2+—few vessels reach the sponge.
3+—many vessels reach the sponge with beginning of penetration in the implant.
4+—very intensive formation of the new vessels with reach and penetration of implant.

After in situ scoring the implant from each animal was cut into two equal portions. The first portion was placed in the plastic vial containing 4% Buffered Formalin (for histological sections and further microscopical examination), the second one was measured for hemoglobin concentration.

Whole Mount Staining of the Aortic Rings

For whole mount Smooth Muscle Actin (SMA) FITC staining:
(1) Fixation with 1% paraformaldehyde for 30 min.
(2) Rinsing with PBS overnight.
(3) Block with PBS+1% BSA overnight+tritonX 100 0.01%.
(4) Incubate with rat anti-mouse CD31 (BD PharMingen Catalogue 01951D, rat monoclonal anit-pecam, clone MEC13.3.) 1:500 dilution overnight.
(5) Wash with PBS×3 times. Time over 8-10 hrs.

ABCAM mouse monoclonal to alpha actin (SMA) (FITC) Clone 1A4 ab8211-100 lot: 8393 ABCAM Ltd, Cambridge.
Cell culture and transfection.

HEK293 Cells

The HEK293 cells were grown in Dulbecco's Modified Eagle's medium (DMEM) with 4 mM L-glutamine, supplemented with 10% horse serum in a 37° C. humidified incubator with 5% CO2. HEK293 cells were transfected using the fuGENE 6 Transfection Reagent. The following amounts of each expression plasmid were used for transfection of each well in a 6-well culture plate: 3 ug of pBK-flag β2AR; 3 ug of pRK5-GRK2 or in combination of 1.5 ug of pBK-flag β2AR and pRK5-GRK2. Cells were harvested after 24 h and transferred into 96-well culture plate (105 cells/ml) and a cAMP assay was carried out 48 h post transfection.

B16 melanocyet cells were grown in DMEM with 4 mM L-glutamine, supplemented with 10% bovine calf serum in a 37° C. humidified incubator with 5% CO2. The day before the assays, 100 μl of $3\times10^4$ cells/ml were plated in 96-well microtiter plates overnight.

3T3L1 Adipocytes Cells

3T3L1 fibroblast were maintained in DMEM with 4 mM L-glutamine, supplemented with 10% calf serum in a 37° C. humidified incubator with 5% $CO_2$. To differentiate fibroblast into adipocytes, cells were grown for 2 days after confluence. The media was then changed to DMEM containing 10% fetal bovine serum; 0.5 mM isobutylmethlxanthine; 4 μg/ml dexamethasone. 3 days later cells were maintained in DMEM containing 10% fetal bovine serum for two weeks, after which the cells were used for cAMP assay.

cAMP Assay

At the day of the assay medium was replaced with serum free medium containing 0.5 mM 3-isobutyl-methylxanthine and the experimental peptides were added for 60 min. The incubation was stopped by replacing the medium with lysis regent supplied in a commercial cAMP kit.

cAMP levels were determined using cAMP enzymeimmunoassay (EIA) system Biotra Amersham Pharmacia Biotech.

Melanogenesis

The day after B16 cells culturing, differential concentrations of stimulator (peptides or αMSH as positive control) were added. The cells were incubated for another 3 days then adding 70 ul of 1N NaOH stopped the reaction. The production of melanin was measured after 24 h as the optical absorbance in 405 nM.

Peptides Formulation.

"tbi" Formulation: peptides (10 mM final) were dissolved in DMSO (final 8%) and 2M Ammonium Bicarbonate (32% final) were added, the mixture was heated for 40 min then 2M HEPES pH 7.5 60% (final) were added.

"shs" Formulation: peptides (10 mM final) were dissolved in 4 ul of DMSO (final 4%) and 6 ul of 66% glycerol (6% final) and 90 ul of 2% solutol were added. Different dilutions in medium or Phosphate buffer saline were used to stimulate the cells.

Example 3

Modulation of Angiogenesis in Aortic Ring Assay by the Compounds of the Invention Aortic ring assay was performed as described above in "Experimental Procedures" with compounds comprising the peptide of the invention R002L103.

FIG. 3 shows pictures of aortic rings incubated with sphingosine 1 phosphate 100 nm, with 10 μm and 20 μm R002L103. As can be seen the compound of the invention was able to increase angiogenesis in a dose dependent manner, in a degree at least equal to that of S1P, EDG3's natural agonist.

Figure 2A:
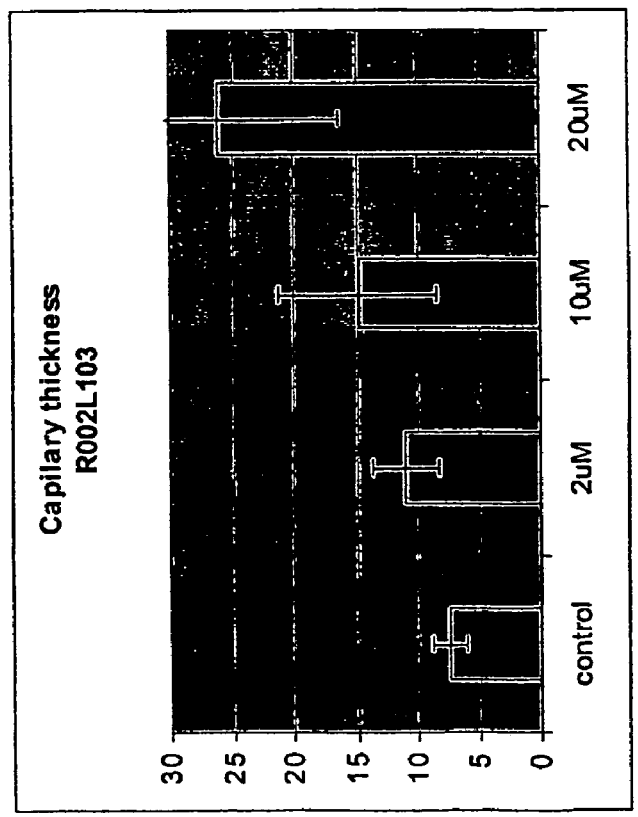
Figure 3A:
FIGS. 3A-3D show an aortic ring in the absence of any compound (FIG. 3A) in the presence of EDG3's natural agonist sphingosine-1-phosphate (S1P) 100 nM (FIG. 3B) and with 10 μM and 20 μM of the compound of the invention R002L103 (FIGS. 3C and 3D respectively).
Figure 3B:
Figure 3C:
Figure 3D:
Figure 4A:
FIGS. 4A-4D shows an aortic ring picture of EDG3's natural agonist S1P 100 nM (FIGS. 4A and 4B) and the compound of the invention (FIGS. 4C and 4D) in the absence (FIGS. 4A and 4C) or presence (FIGS. 4B and 4D) of the G-protein inhibitor pertussis toxin (PTX) 100 nM/ml.
Figure 4B:
Figure 4D:
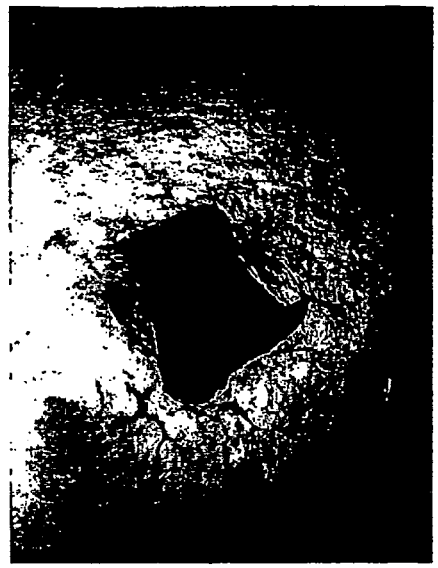
Figure 4C:

FIG. 2 shows a graph indicating a capillary thickness and capillary length in the presence and absence of various concentrations of R002L103. As can be seen, capillary thickness was directly correlated to the concentration of the compound of the invention, while capillary length, was increased from control to 10 μm of the compound, and decreased in 20 μm, probably as compensation for the increased thickness of the capillary.

FIG. 4 shows that the stimulatory effect of R002L103 and S1P on an aortic ring neovascularization is dependent on G-protein, as in the presence of S1P 100 μm, and R002L103 20 μm, caused neovascularization, which was completely blocked by the G-protein inhibitor pertussis toxic (PTX) 100 nm/ml.

Figure 5B:
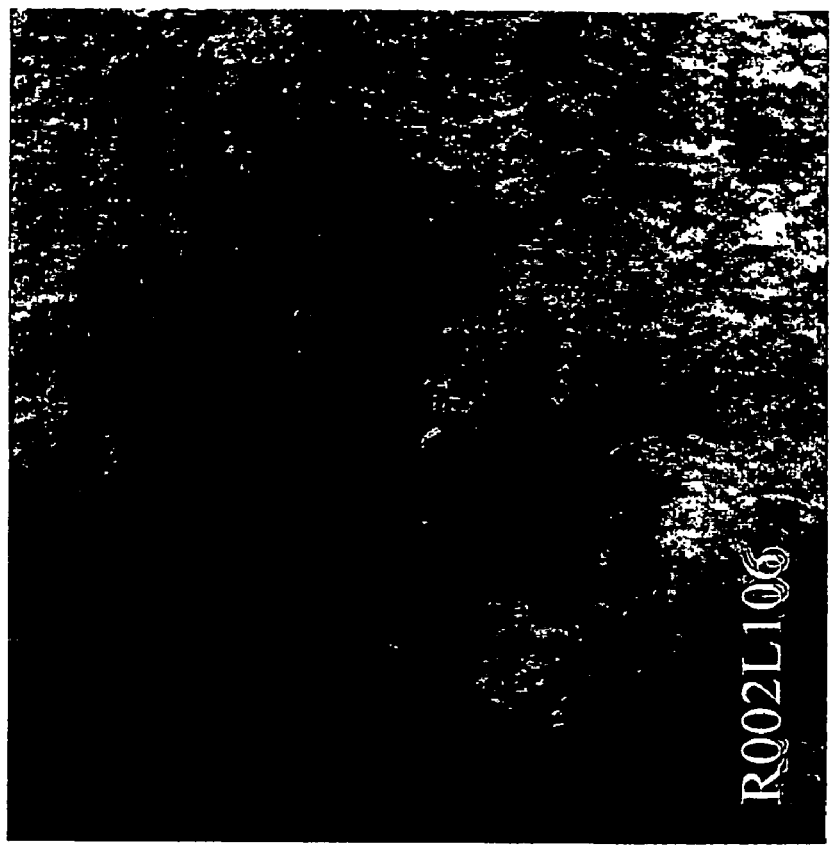
FIGS. 5A and 5B show a cross section of an aortic ring in the absence (FIG. 5A) and presence (FIG. 5B) of 20 μM of the compound of the invention R002L106.
Figure 5A:
Figure 6B:
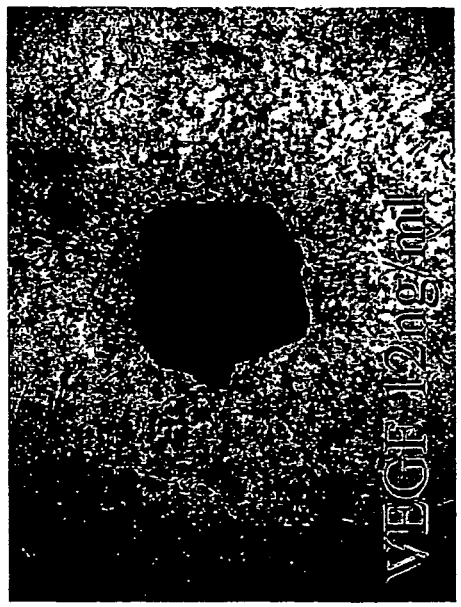
FIG. 6A is the control and FIGS. 6B and 6C are VEGF and R002L103 alone.
Figure 6D:
FIG. 6D shows a synergistic effect of the compound of the invention R002L103 and VEGF.
Figure 6A:
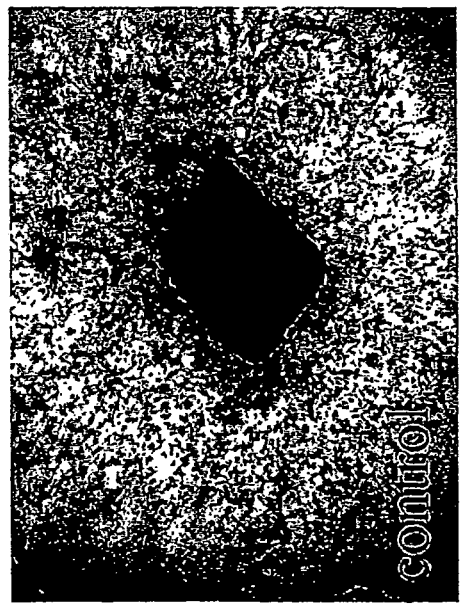
Figure 6C:
Figure 7A:
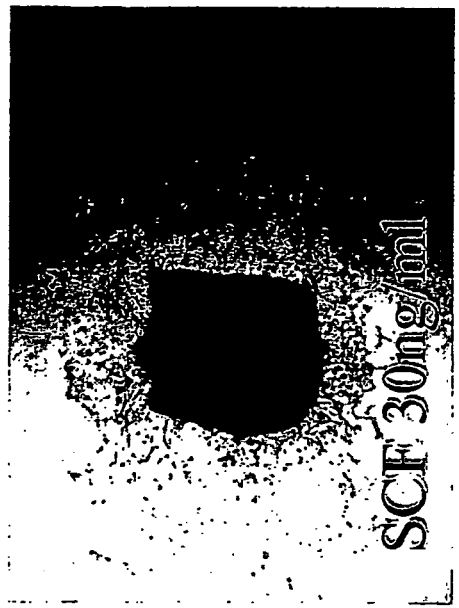
FIG. 7A is the control and FIGS. 7B and 7C are SCF and R002L103 alone.
Figure 7B:
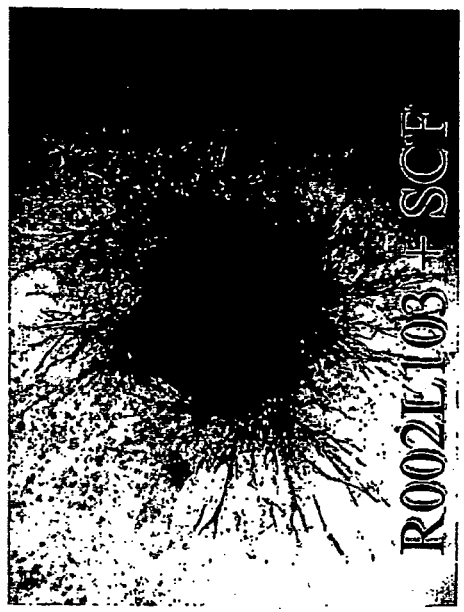
Figure 7C:
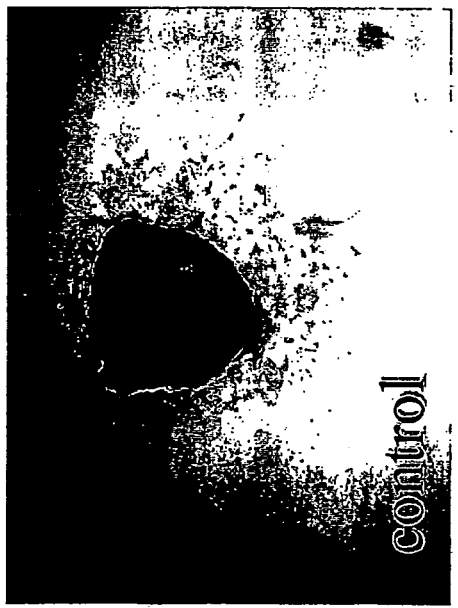
Figure 7D:
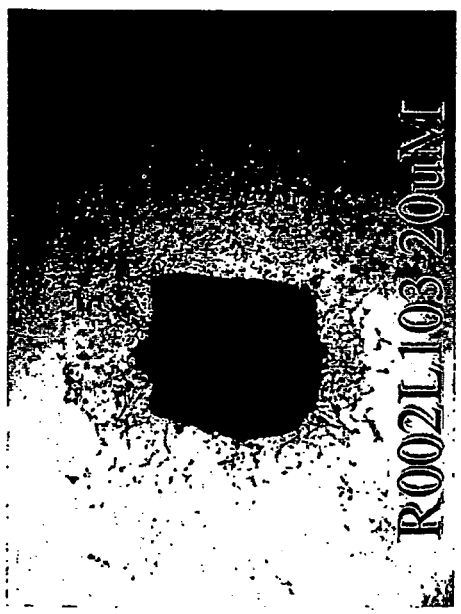
FIG. 7D shows a synergistic effect of the compound of the invention R002L103 and SCF.

FIG. 5 shows a small cross section of an aortic ring in the absence (control) and in the presence of 20 μm of R002L106. As can be seen, there is a significant difference in the neo-capillarization induced in the absence and presence of the compound of the invention R002L106.

Example 4

Synergistic Effect of the Compounds of the Invention with Various Pro-Angiogenesis Compounds The above procedure of neovascularization in aortic rings was repeated in the presence of lower amounts of the compound of the invention, and at least one additional pro-angiogenetic compound.

FIG. 6 shows a synergistic effect of the compound of the invention R002L103, and VEGF, as with 12 nm/ml of VEGF, and 20 μg of R002L103, there was hardly any angiogenetic effect, while the combination of the two, in these concentrations caused a marked and significant neovascularization process. A synergistic effect was also tested with another pro-angiogenetic compound (FIG. 7) SCF and again it can be seen that while SCF 30 nm/ml and the compound of the invention R002L103 20 μg had no neovascularization effect separately, together they showed a marked synergism and significant neovascularization.

The same experiment was repeated again with FGF, and as can be seen in FIG. 8, 10 ng/ml of FGF, and 20 μg of R002L103 separately showed no effect, while their combination showed a very significant neovascularization.

Example 5

Figure 10B:
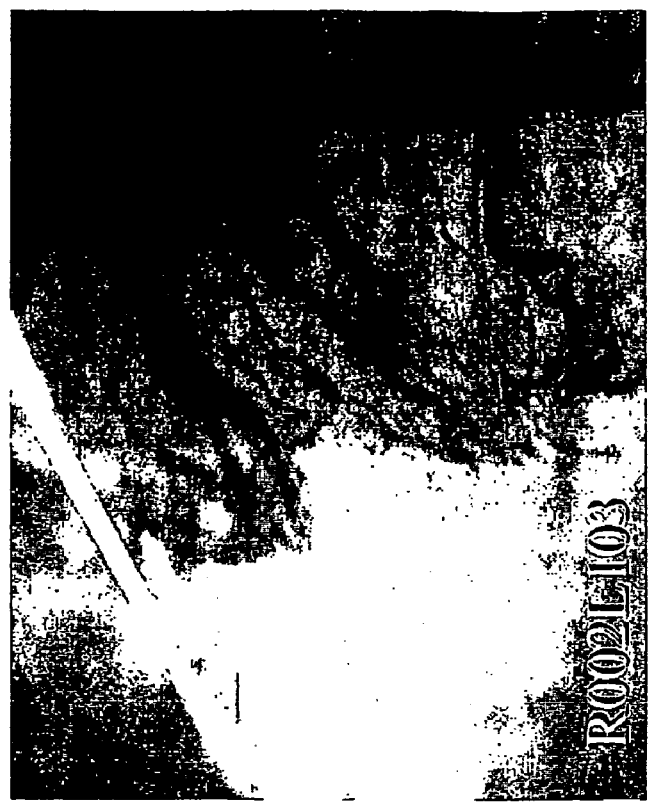
FIGS. 10A and 10B show a smaller section of the blood vessels of FIGS. 9B and 9C.
Figure 10A:

In Vivo Modulation of Angiogenesis in the Eye by the Compounds of the Invention The eye assay was performed as detailed in "Experimental Procedures" and the results are shown in FIG. 9. As can be seen, both VEGF and R002L103 were able to induce neovascularization in the eye and response to implantation of a pellet, where the compound of the invention caused a marked neovascularization (as evident by a larger number of blood vessels as compared to VEGF). These results were substantiated as can be seen in FIG. 10, which shows the eye assay results five days after implantation, wherein in VEGF the blood vessels course of growth was more coiled, as compared to the relatively straight new blood vessels grown in the presence of the compound of the invention R002L103.

Example 6

Figure 11:
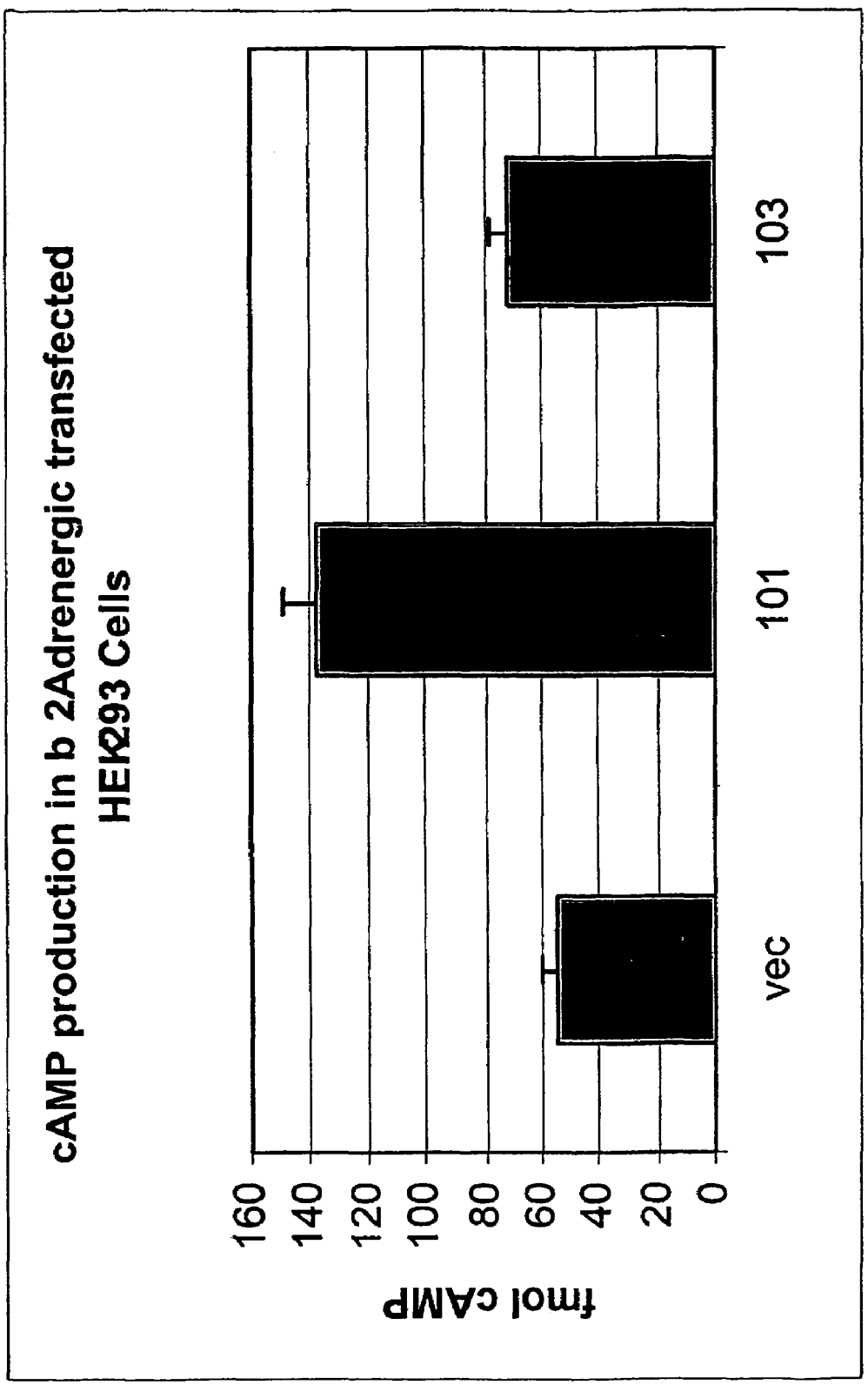
FIG. 11 shows the effects of a compound of the invention comprising a β3-adrenergic derived sequence (R013L101 and R013L103) on cAMP production in HEK293 cells.
Figure 12:
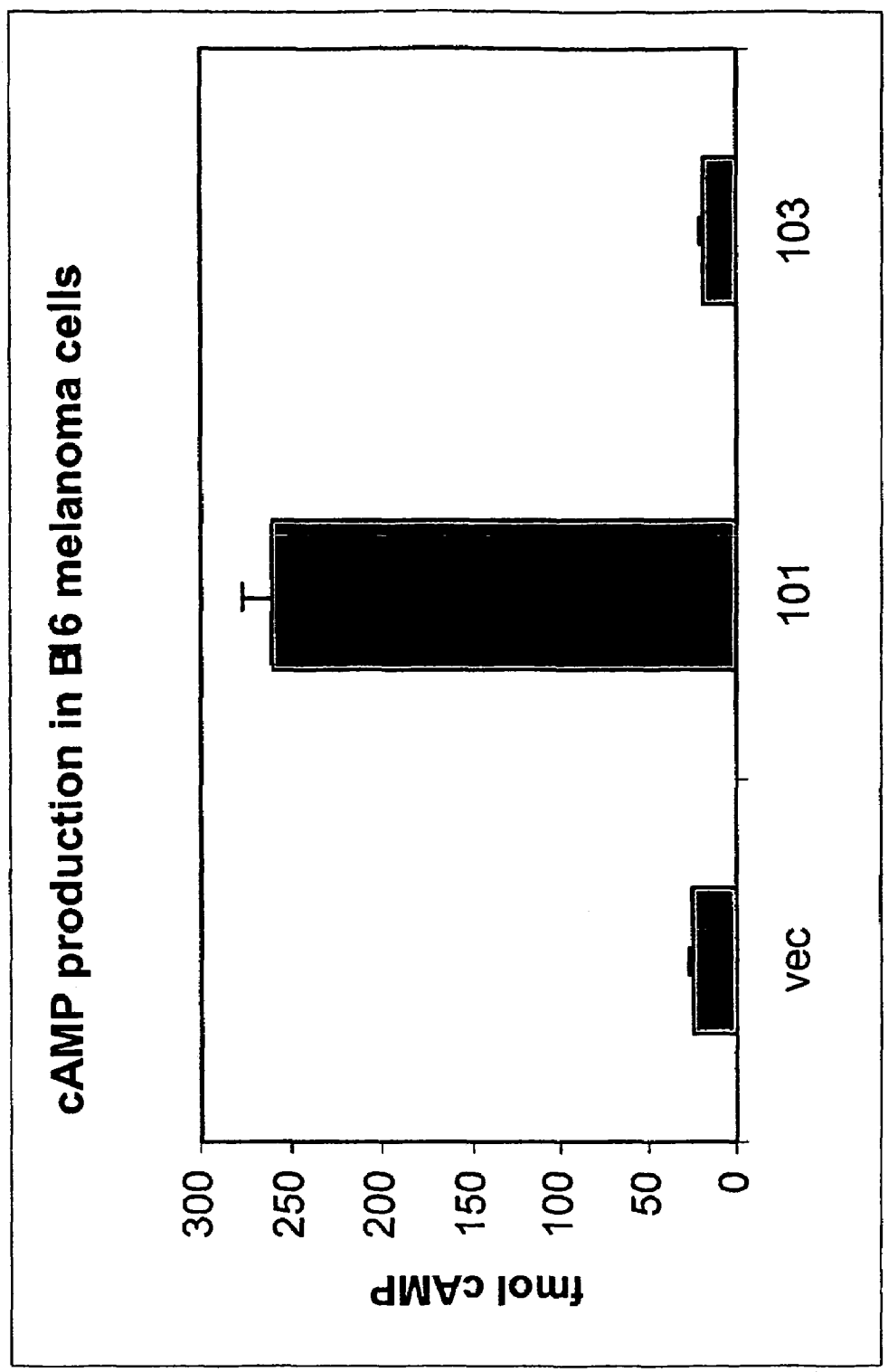
FIG. 12 shows the effects of a compound of the invention comprising a β3-adrenergic derived sequence (R013L101 and R013L103) on cAMP production in B16 melanoma cells.

Effect of the Compounds of the Invention Derived from Beta Receptor cAMP Production β2-adrenergic transfected HEK293 cells and B16 cells were stimulated with or without 10 μM of R013L101 or R013L103 (β3-adrenergic Loop 2 derived peptides). After 1 h the production of cAMP was measured, the results are presented in FIG. 11 and FIG. 12. R013L101 peptide significantly increases the cAMP production in both cells comparing to the control level (HEK293 140% and B16 900%). In contrast R013L103 peptide did not affect the cAMP production comparing to the control group.

Figure 13:
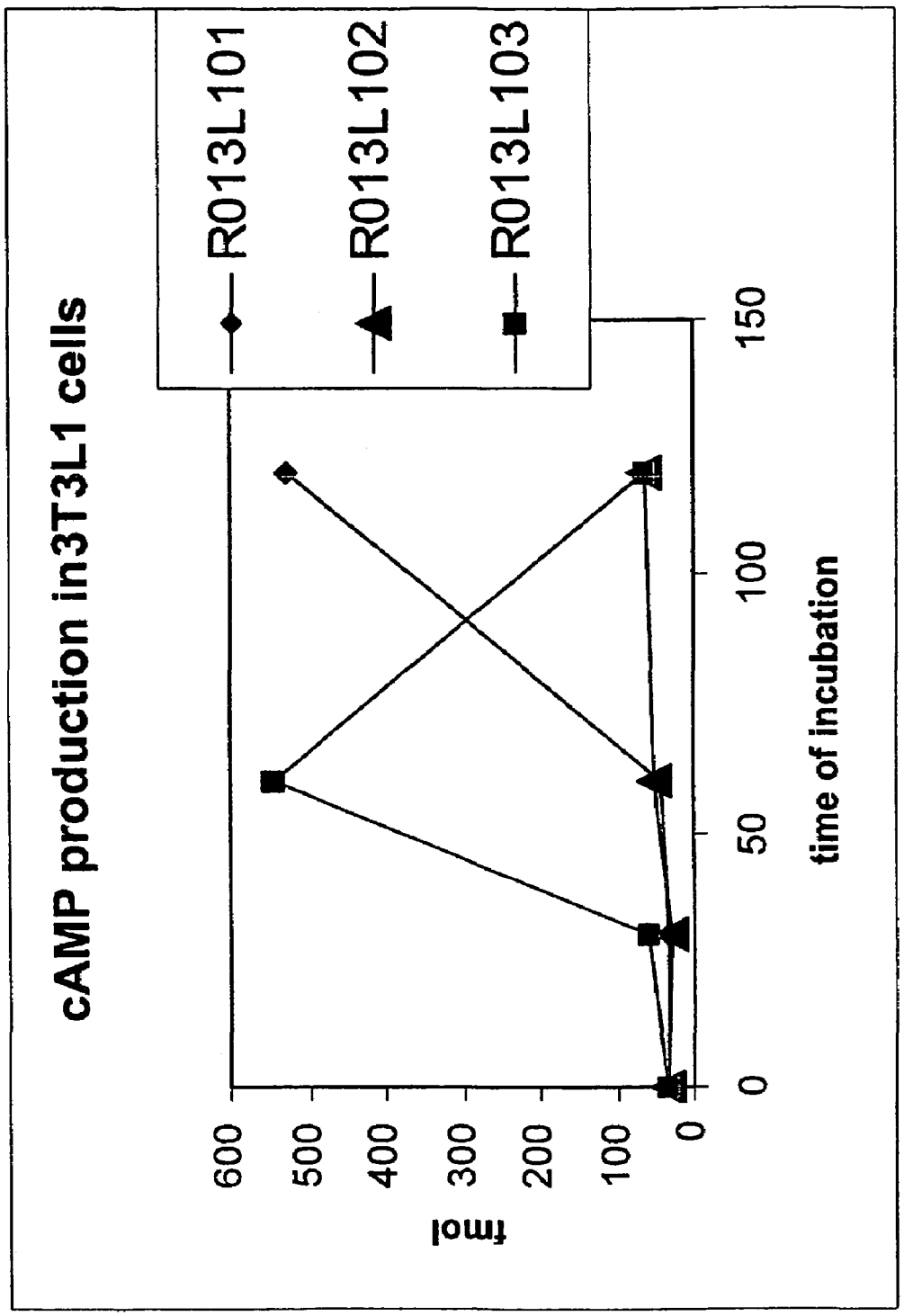
FIG. 13 shows the effects of two compounds of the invention comprising a β3-adrenergic derived sequence (R013L101 and R013L103) on cAMP production in 3T3L1 adipocyte cells
Figure 14:
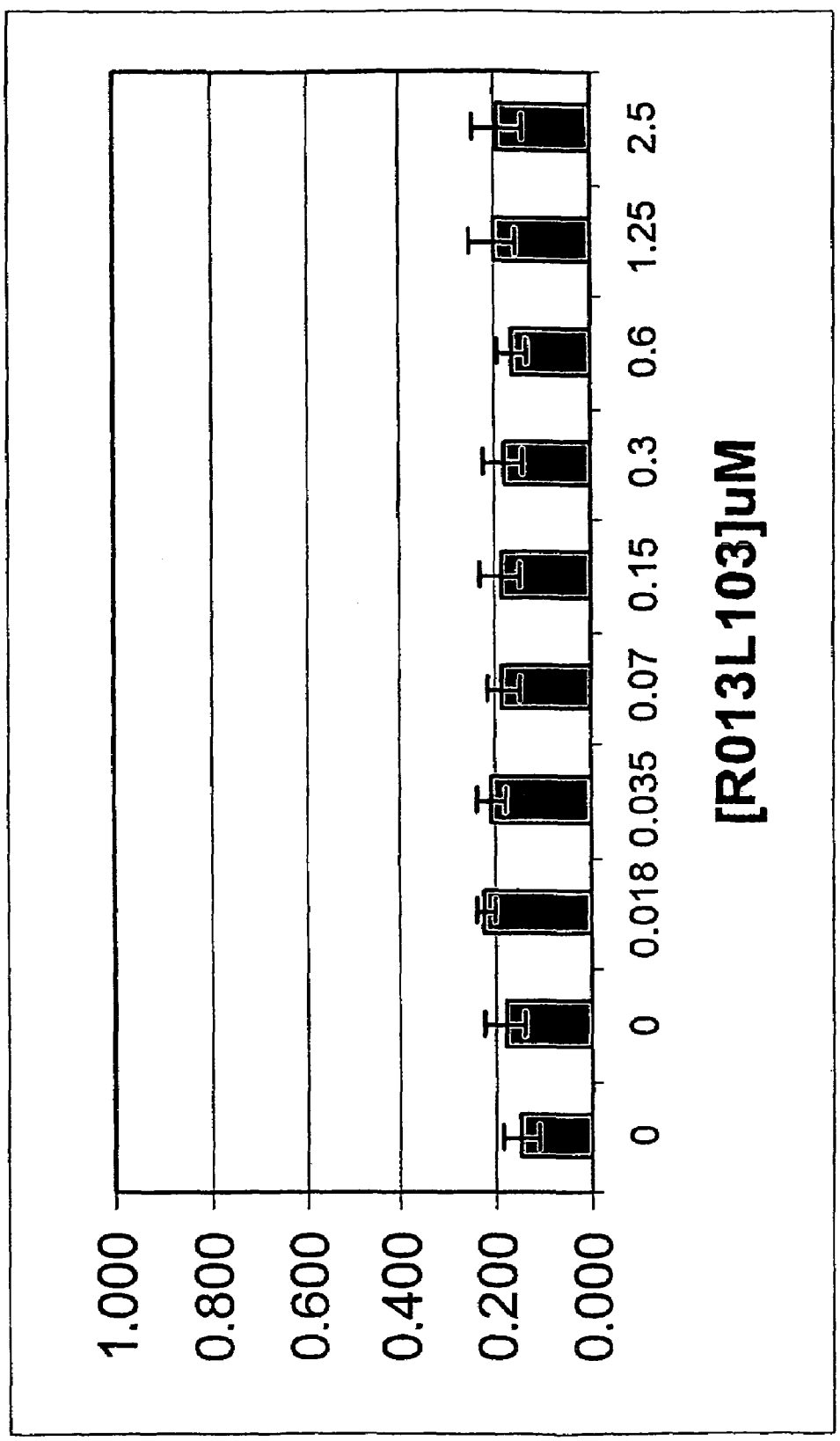
FIGS. 14-18 show the effect of compounds of the invention comprising a β3-adrenergic derived sequence R013L101 (FIG. 15), R013L102 (FIG. 16), and R013L103 (FIG. 14) and MC1 derived modified sequences K024H107 (FIG. 18) and K024H124 FIG. 17), respectively, on melanogenesis in B16 cells.
Figure 15:
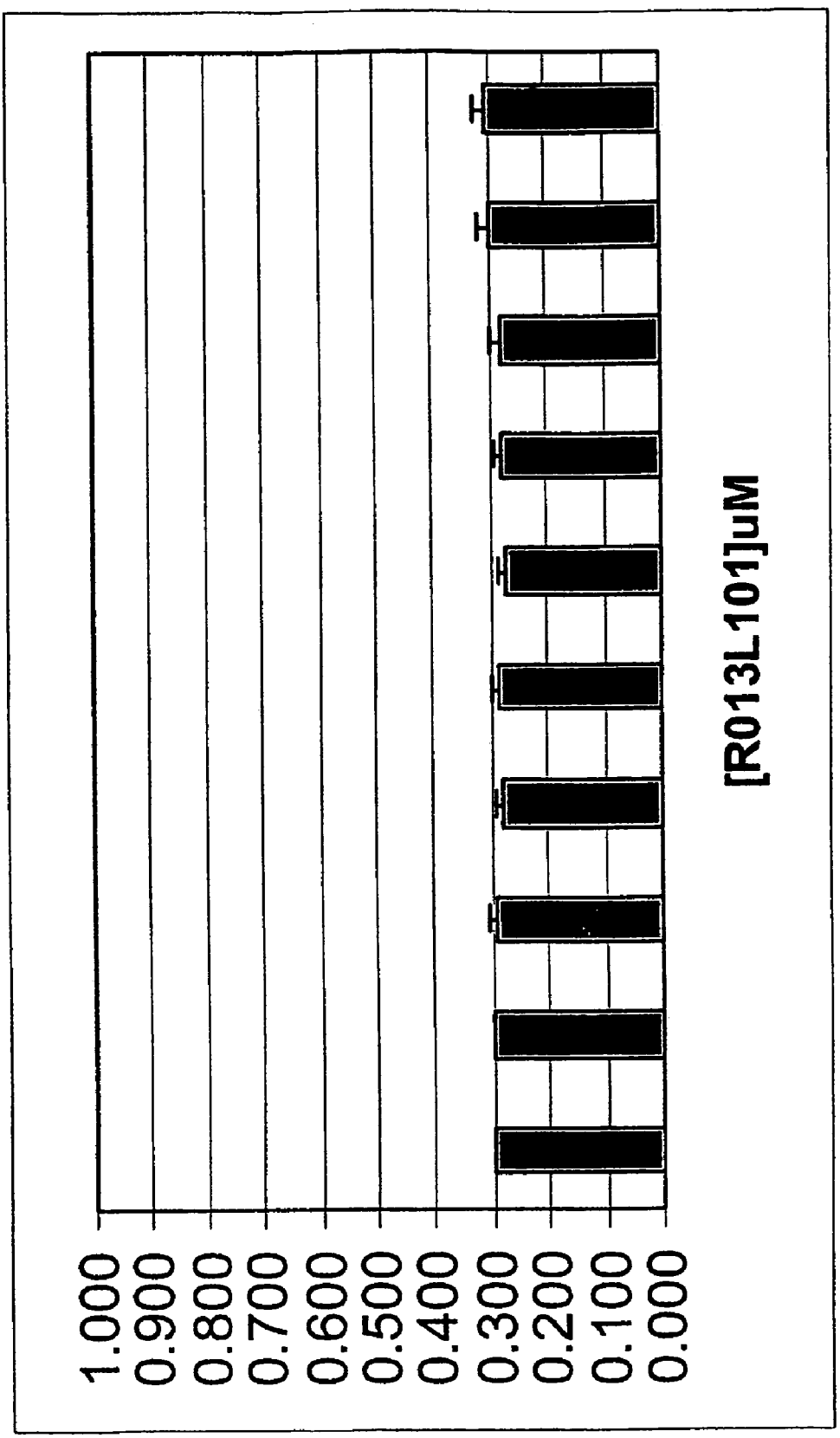
Figure 16:
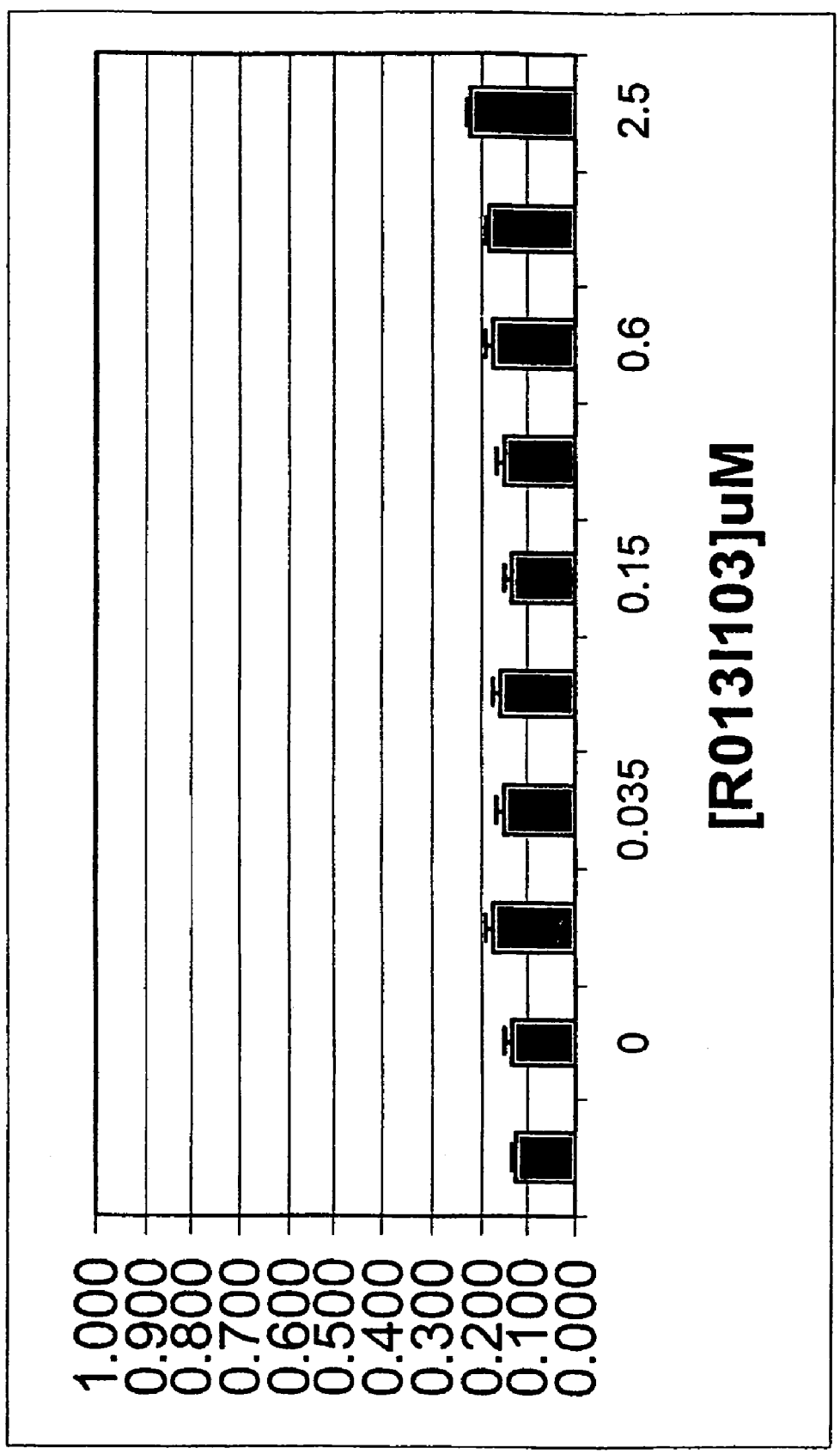
Figure 17:
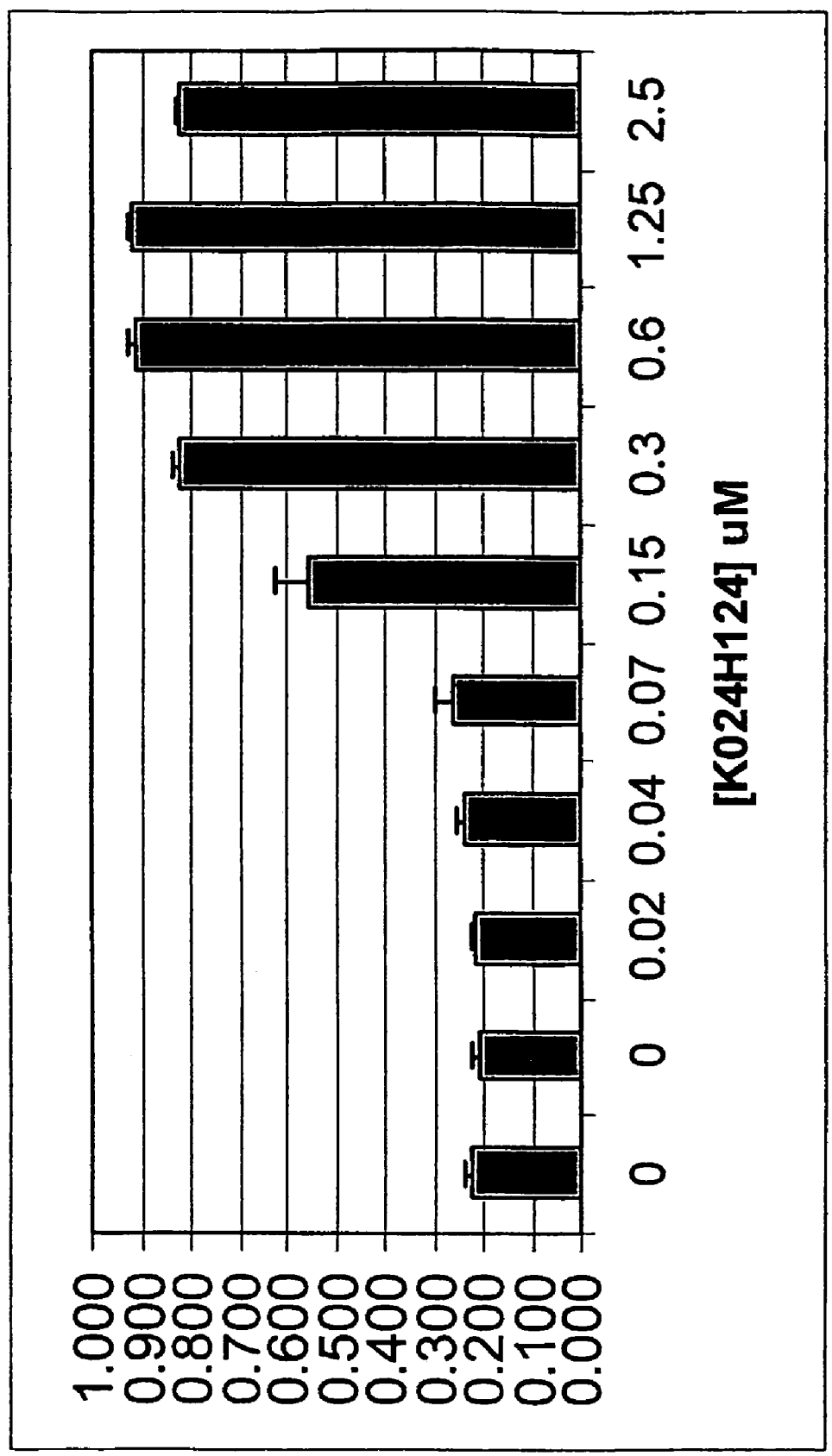
Figure 18:
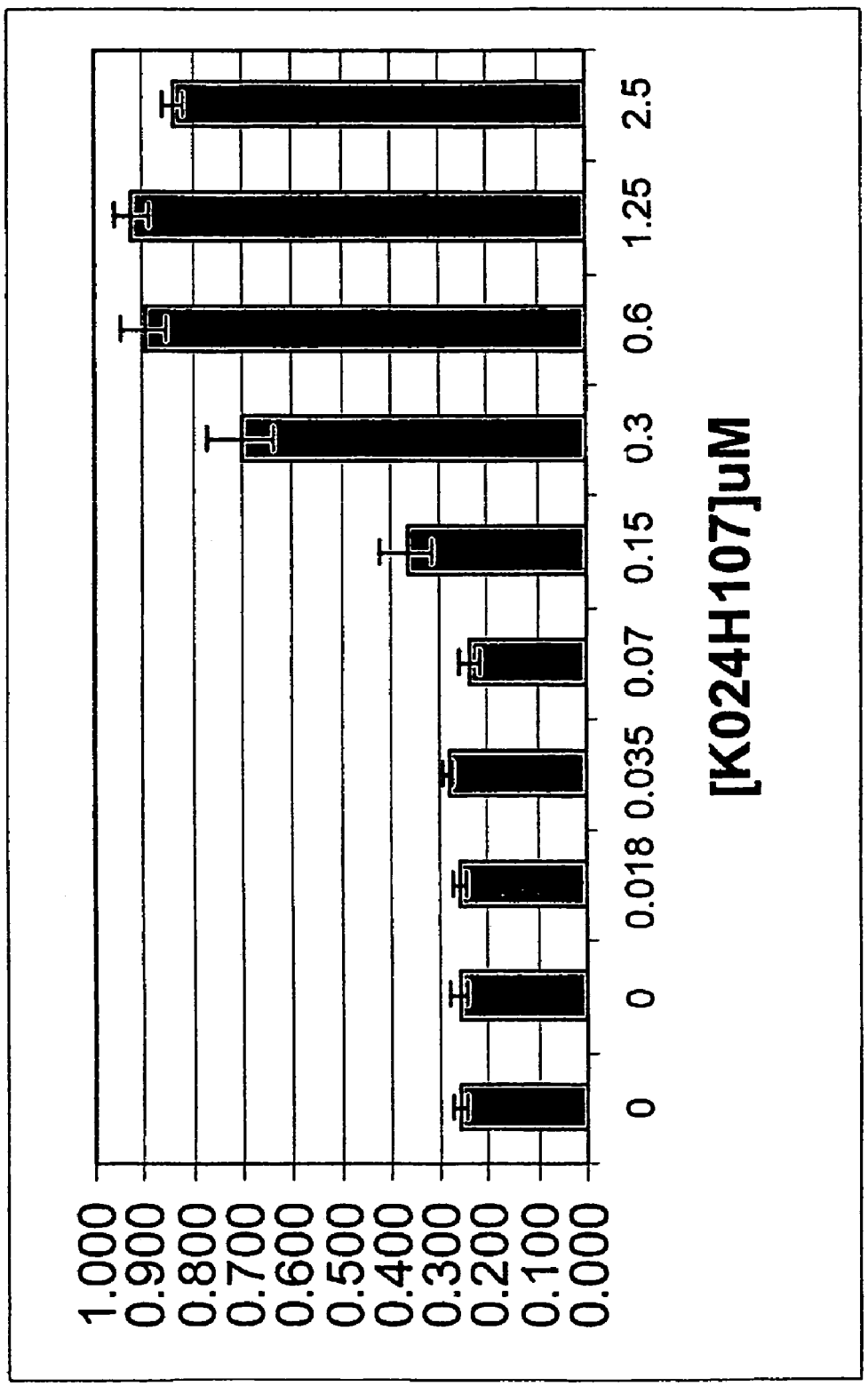

The effect of R013L101, R013L102 and R013L103 (□3-adrenergic Loop 2 derived peptides) on cAMP production in 3T3L1 adipocytes cells was measured after 30, 60 and 120 min of incubation with the peptides. And the results are shown in FIG. 13. The level of cAMP was increased 18 fold in response to incubation with R013L101 and R013L103 after 60 or 120 min respectively. In contrast R013L102 did not affect the cAMP production even after 120 min of incubation.

Example 7

The Effect of the Compounds of the Invention on Melanogenesis

The Melanogenesis activity of R013L101, R013L102 and R013L103 (β3-adrenergic receptor, Loop 2 derived peptides) in tbi formulation or K024H107 and K024H124 (MC1 receptor Loop 2 derived-modified peptides) in tbi formulation is studied in B16 cells and the results are presented in FIG. 14-18. The results of melanogenesis are clearly demonstrated that MC1 receptor derived peptides are very efficient in inducing melanogenesis in B16 cells (EC 50 for K024H107 02 μM and for K024H124 0.15 μM, FIG. 7-8). In contrast, the β3-adrenergic receptor derived peptides failed as melanogenesis inducers in B16 cells, even in high concentration of the peptide (2.5 μM).

The results presented here suggest that compounds comprising sequences derived from the MC1 receptor can modulated 7TM-receptor signal transduction.

---

What is claimed is:

1. A compound which has the property of modulation of signal transduction of a seven transmembrane (7TM) receptor consisting of: at least one moiety for transport across cellular membranes, in association with a peptide sequence of 5-20 amino acid residues selected from the group consisting of:
   (a) a peptide sequence which is a continuous stretch of at least 5 amino acids present in the 7TM receptor in positions corresponding to the positions 143-151 of bovine rhodopsin when the $2^{nd}$ intracellular region of the 7TM receptor is aligned with the $2^{nd}$ intracellular region of rhodopsin;
   (b) a variant of the peptide sequence according to (a) wherein up to 40% of the amino acids of the native sequence have been replaced with a naturally or non-naturally occurring amino acid or with a peptidomimetic moiety; and/or up to 40% of the amino acids have their side chains chemically modified; and/or up to 20% of the amino acids have been deleted, provided that, when the $2^{nd}$ intracellular region of the 7TM receptor is aligned with the corresponding $2^{nd}$ intracellular region of bovine rhodopsin, at least 50% of the amino acids corresponding to positions 143-151 of parent bovine rhodopsin sequence of (a) are maintained unaltered in the variant;
   (c) a peptide sequence according to (a) or (b) wherein at least one of the amino acids is replaced with a corresponding D-amino acid;
   (d) a peptide sequence according to any one of (a)-(c) wherein at least one of the peptidic backbones has been altered to a non-naturally occurring peptidic backbone;
   (e) a peptide sequence being the sequence of any one of (a)-(d) in reverse order; and
   (f) a combination of two or more of the peptide sequences of (a) to (e).

2. A compound according to claim 1, wherein the moiety is a hydrophobic moiety.

3. A pharmaceutical composition comprising as an active ingredient at least one of the compounds of claim 1.

4. A pharmaceutical composition according to claim 3 comprising as an active ingredient a peptide sequence selected from the group consisting of SEQ ID NO:4, SEQ ID NO:5, SEQ ID NO:7, SEQ ID NO:8, SEQ ID NO:9, SEQ ID NO:10, SEQ ID NO:11, SEQ ID NO:12, and SEQ ID NO:13.

5. A compound according to claim 1, wherein the peptide sequence is selected from the group consisting of SEQ ID NO:4, SEQ ID NO:5, SEQ ID NO:7, SEQ ID NO:8, SEQ ID NO:9, SEQ ID NO:10, SEQ ID NO:11, SEQ ID NO:12, and SEQ ID NO:13.

6. The compound according to claim 1, wherein the peptide sequence consists of 5-9 amino acid residues.

7. The compound according to claim 6, comprising a peptide sequence is selected from the group consisting of SEQ ID NO:4, SEQ ID NO:5, SEQ ID NO:8, SEQ ID NO:9, SEQ ID NO:10, SEQ ID NO:11, SEQ ID NO:12, and SEQ ID NO:13.

8. The compound according to claim 1, wherein the 7TM receptor is endothelial differentiation gene 3 (EDG3).

9. The compound according to claim 8, wherein the peptide sequence of 5-20 amino acid residues is selected from the group consisting of:
   (a) a continuous stretch of at least 5 amino acids present in native EDG3 in positions 135-154;
   (b) a variant of the peptide sequence according to (a) wherein up to 40% of the amino acids of the native sequence have been replaced with a naturally or non-naturally occurring amino acid or with a peptidomimetic moiety; and/or up to 40% of the amino acids have their side chains chemically modified; and/or up to 20% of the amino acids have been deleted provided that at least 50% of the amino acids in positions 135-154 of parent EDG3 sequence of (a) are maintained unaltered and the variant
   (c) a peptide sequence according to (a) or (b) wherein at least one of the amino acids is replaced with a corresponding D-amino acid;
   (d) a peptide sequence according to any one of (a)-(c) wherein at least one of the peptidic backbones has been altered to a non-naturally occurring peptidic backbone;
   (e) a peptide sequence being the sequence of any one of (a)-(d) in reverse order; and
   (f) a combination of two or more of the peptide sequences of (a) to (e).

10. The compound according to claim 9, wherein the peptide sequence consists of 5-9 amino acid residues.

11. The compound according to claim 10, wherein the peptide sequence of 5-9 amino acid residues is selected from SEQ ID NO:4 and SEQ ID NO:5.

12. The compound according to claim 1, wherein the 7TM receptor is $\beta$2-adrenoreceptor.

13. The compound according to claim 12, wherein the peptide sequence of 5-20 amino acid residues is selected from the group consisting of SEQ ID NO:7, SEQ ID NO:8 and SEQ ID NO:9.

14. The compound according to claim 1, wherein the 7TM receptor is melanocortin 1 (MC1).

15. The compound according to claim 14, wherein the peptide sequence consists of 5-9 amino acid residues.

16. The compound according to claim 15, wherein the peptide sequence is selected from the group consisting of SEQ ID NO:10, SEQ ID NO:11, SEQ ID NO:12 and SEQ ID NO:13.

* * * * *

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial
<220> FEATURE:
<223> OTHER INFORMATION: synthetic

<400> SEQUENCE: 1

Met Arg Pro Tyr Asp Ala Asn Lys Arg
1               5

<210> SEQ ID NO 2
<211> LENGTH: 9
<212> TYPE: PRT
<213> ORGANISM: Artificial
<220> FEATURE:
<223> OTHER INFORMATION: synthetic
```

<400> SEQUENCE: 2

Arg Lys Asn Ala Asp Tyr Pro Arg Met
1               5

<210> SEQ ID NO 3
<211> LENGTH: 19
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: EDG3

<400> SEQUENCE: 3

Glu Arg His Leu Thr Met Ile Lys Met Arg Pro Tyr Asp Ala Asn Lys
1               5                   10                  15

Arg His Arg

<210> SEQ ID NO 4
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: R002L103

<400> SEQUENCE: 4

Met Arg Pro Tyr Asp Ala Asn Lys Arg
1               5

<210> SEQ ID NO 5
<211> LENGTH: 6
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: R002L106
<220> FEATURE:
<221> NAME/KEY: misc_feature
<222> LOCATION: (1)..(1)
<223> OTHER INFORMATION: Xaa is Nle

<400> SEQUENCE: 5

Xaa Arg Pro Tyr Asn Ala
1               5

<210> SEQ ID NO 6
<211> LENGTH: 20
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: Lop 2 b3-Adr

<400> SEQUENCE: 6

Asp Arg Tyr Leu Ala Val Thr Asn Pro Leu Arg Tyr Gly Ala Leu Val
1               5                   10                  15

Thr Lys Arg Cys
            20

```
<210> SEQ ID NO 7
<211> LENGTH: 11
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: R013L101
<220> FEATURE:
<221> NAME/KEY: misc_feature
<222> LOCATION: (1)..(1)
<223> OTHER INFORMATION: Gly is modified with a myristoyl group.

<400> SEQUENCE: 7

Gly Asn Pro Leu Arg Tyr Gly Ala Leu Val Thr
1               5                   10

<210> SEQ ID NO 8
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: R013L102
<220> FEATURE:
<221> NAME/KEY: misc_feature
<222> LOCATION: (1)..(1)
<223> OTHER INFORMATION: Gly is modified with a myristoyl group.

<400> SEQUENCE: 8

Gly Leu Arg Tyr Gly Ala Leu Val Thr Lys
1               5                   10

<210> SEQ ID NO 9
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: R013L103
<220> FEATURE:
<221> NAME/KEY: misc_feature
<222> LOCATION: (1)..(1)
<223> OTHER INFORMATION: Gly is modified with a myristoyl group.

<400> SEQUENCE: 9

Gly Pro Leu Arg Tyr Gly Ala Leu Val Thr
1               5                   10

<210> SEQ ID NO 10
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: R001L115
<220> FEATURE:
<221> NAME/KEY: misc_feature
<222> LOCATION: (1)..(1)
<223> OTHER INFORMATION: Gly is modified with a myristoyl group.

<400> SEQUENCE: 10

Gly Leu Arg Tyr His Ser Ile Val Thr
1               5
```

```
<210> SEQ ID NO 11
<211> LENGTH: 10
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: R001L116
<220> FEATURE:
<221> NAME/KEY: misc_feature
<222> LOCATION: (1)..(1)
<223> OTHER INFORMATION: Gly is modified with a myristoyl group.

<400> SEQUENCE: 11

Gly Leu Arg Tyr His Ser Ile Val Lys Thr
1               5                   10

<210> SEQ ID NO 12
<211> LENGTH: 7
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: K024H107
<220> FEATURE:
<221> NAME/KEY: misc_feature
<222> LOCATION: (1)..(1)
<223> OTHER INFORMATION: Gly is modified with a myristoyl group.

<400> SEQUENCE: 12

Gly Leu Leu Arg Arg His Ser
1               5

<210> SEQ ID NO 13
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: misc_feature
<223> OTHER INFORMATION: K024H124

<400> SEQUENCE: 13

Leu Gly Leu Leu Arg Arg His Ser Ile
1               5
```